(12) United States Patent
Wood et al.

(10) Patent No.: US 6,552,179 B1
(45) Date of Patent: Apr. 22, 2003

(54) MUTANT LUCIFERASES

(75) Inventors: Keith V. Wood; Monika G. Gruber, both of Madison, WI (US)

(73) Assignee: Promega Corporation, Madison, WI (US)

(*) Notice: Subject to any disclaimer, the term of this patent is extended or adjusted under 35 U.S.C. 154(b) by 0 days.

(21) Appl. No.: 08/478,205

(22) Filed: Jun. 7, 1995

Related U.S. Application Data

(63) Continuation-in-part of application No. 08/177,081, filed on Jan. 3, 1994, now abandoned.

(51) Int. Cl.$^7$ .............................. C12N 15/53; C12N 9/02
(52) U.S. Cl. ................... 536/23.2; 435/189; 435/252.3; 435/320.1
(58) Field of Search .................... 536/23.2; 435/189, 435/172.3, 252.3, 320.1

(56) References Cited

PUBLICATIONS

Wood, "Luciferases of Luminous Beetles: Evolution, Color Variation, and Applications", Dissertation, 1989.

Wood, et al., "Complementary DNA Coding Click Beetle Luciferases Can Elicit Bioluminescence of Different Colors", *Science*, vol. 244, pp. 700–702, May, 1989.

Wood, "Luc Genes: Introduction of Colour into Bioluminescence Assays", *Journal of Bioluminescence and Chemiluminescence*, vol. 5, pp. 107–114, 1990.

Wood, et al., "Bioluminescent Click Beetles Revisited", *Journal of Bioluminescence and Chemiluminescence*, vol. 4, pp. 31–39, Jul., 1989.

Wood, et al., "Introduction to Beetle Luciferases and their Applications", *Journal of Bioluminescence and Chemiluminescence*, vol. 4, pp. 289–301, Jul., 1989.

Kajiyama, et al., "Isolation and characterization of mutants of firefly luciferase which produce different colors of light", *Protein Engineering*, vol. 4, No. 6, pp. 691–693, 1991.

Sala–Newby, et al., "Engineering a bioluminescent indicator for cyclic AMP–dependent protein kinase", *Biochem. J.*, vol. 279, pp. 727–732, Nov. 1991.

Sala–Newby, et al., "Engineering firefly luciferase as an indicator of cyclic AMP–dependent protein kinase in living cells", FEBS Letters, vol. 307, No. 2, pp. 241–244, Jul., 1992.

International Search Report for PCT Application No. PCT/US95/00108, corresponding to United States Patent Application No. 08/177,081.

*Primary Examiner*—Rebecca E. Prouty
(74) *Attorney, Agent, or Firm*—Schwegman, Lundberg, Woessner & Kluth, P.A.

(57) ABSTRACT

The invention provides active, non-naturally occurring mutants of beetle luciferases and DNAs which encode such mutants. A mutant luciferase of the invention differs from the corresponding wild-type luciferase by producing bioluminescence with a wavelength of peak intensity that differs by at least 1 nm from the wavelength of peak intensity of the bioluminescence produced by the wild-type enzyme. The mutant luciferases and DNAs of the invention are employed in various biosensing applications.

30 Claims, No Drawings

MUTANT LUCIFERASES

This application is a continuation-in-part of application Ser. No. 08/177,081, filed Jan. 3, 1994, now abandoned.

TECHNICAL FIELD

This invention generally relates to luciferase enzymes that produce luminescence, like that from fireflies. More particularly, the invention concerns mutant luciferases of beetles. The mutant luciferases of the invention are made by genetic engineering, do not occur in nature, and, in each case, include modifications which cause a change in color in the luminescence that is produced. The luciferases of the invention can be used, like their naturally occurring counterparts, to provide luminescent signals in tests or assays for various substances or phenomena.

BACKGROUND OF THE INVENTION

The use of reporter molecules or labels to qualitatively or quantitatively monitor molecular events is well established. They are found in assays for medical diagnosis, for the detection of toxins and other substances in industrial environments, and for basic and applied research in biology, biomedicine, and biochemistry. Such assays include immunoassays, nucleic acid probe hybridization assays, and assays in which a reporter enzyme or other protein is produced by expression under control of a particular promoter. Reporter molecules, or labels in such assay systems, have included radioactive isotopes, fluorescent agents, enzymes and chemiluminescent agents.

Included in the assay system employing chemiluminescence to monitor or measure events of interest are assays which measure the activity of a bioluminescent enzyme, luciferase.

Light-emitting systems have been known and isolated from many luminescent organisms including bacteria, protozoa, coelenterates, molluscs, fish, millipedes, flies, fungi, worms, crustaceans, and beetles, particularly click beetles of genus Pyrophorus and the fireflies of the genera Photinus, Photuris, and Luciola. In many of these organisms, enzymes catalyze monooxygenations and utilize the resulting free energy to excite a molecule to a high energy state. Visible light is emitted when the excited molecule spontaneously returns to the ground state. This emitted light is called "bioluminescence." Hereinafter it may also be referred to simply as "luminescence."

The limited occurrence of natural bioluminescence is an advantage of using luciferase enzymes as reporter groups to monitor molecular events. Because natural bioluminescence is so rare, it is unlikely that light production from other biological processes will obscure the activity of a luciferase introduced into a biological system. Therefore, even in a complex environment, light detection will provide a clear indication of luciferase activity.

Luciferases possess additional features which render them particularly useful as reporter molecules for biosensing (using a reporter system to reveal properties of a biological system). Signal transduction in biosensors (sensors which comprise a bilogical component) generally involves a two step process: signal generation through a biological component, and signal transduction and amplification through an electrical component. Signal generation is typically achieved through binding or catalysis. Conversion of these biochemical events into an electrical signal is typically based on electrochemical or caloric detection methods, which are limited by the free energy change of the biochemical reactions. For most reactions this is less than the energy of hydrolysis for two molecules of ATP, or about 70 kJ/mole. However, the luminescence elicited by luciferases carries a much higher energy content. Photons emitted from the reaction catalyzed by firefly luciferase (560 nm) have 214 Kj/einstein. Furthermore, the reaction catalyzed by luciferase is one of the most efficient bioluminescent reactions known, having a quantum yield of nearly 0.9. This enzyme is therefore an extremely efficient transducer of chemical energy.

Since the earliest studies, beetle luciferases, particularly that from the common North American firefly species *Photinus pyralis*, have served as paradigms for understanding of bioluminescence. The fundamental knowledge and applications of luciferase have been based on a single enzyme, called "firefly luciferase," derived from *Photinus Rvralis*. However, there are roughly 1800 species of luminous beetles worldwide. Thus, the luciferase of Photinus pyralis is a single example of a large and diverse group of beetle luciferases. It is known that all beetle luciferases catalyze a reaction of the same substrate, a polyheterocyclic organic acid, D-(-)-2-(6'-hydroxy-2'-benzothiazolyl)-$A\Delta^2$-thiazoline -4-carboxylic acid (hereinafter referred to as "luciferin", unless otherwise indicated), which is converted to a high energy molecule. It is likely that the catalyzed reaction entails the same mechanism in each case.

The general scheme involved in the mechanism of beetle bioluminescence appears to be one by which the production of light takes place after the oxidative decarboxylation of the luciferin, through interaction of the oxidized luciferin with the enzyme. The color of the light apparently is determined by the spatial organization of the enzyme's amino acids which interact with the oxidized luciferin.

The luciferase-catalyzed reaction which yields bioluminescence (hereinafter referred to simply as "the luciferase-luciferin reaction") has been described as a two-step process involving luciferin, adenosine triphosphate (ATP), and molecular oxygen. In the initial reaction, the luciferin and ATP react to form luciferyl adenylate with the elimination of inorganic pyro-phosphate, as indicated in the following reaction:

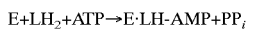
$$E+LH_2+ATP \rightarrow E \cdot LH\text{-}AMP+PP_i$$

where E is the luciferase, $LH_2$ is luciferin, and PPi is pyrophosphate. The luciferyl adenylate, $LH_2$-AMP, remains tightly bound to the catalytic site of luciferase. When this form of the enzyme is exposed to molecular oxygen, the enzyme-bound luciferyl adenylate is oxidized to yield oxyluciferin (L=O) in an electronically excited state. The excited oxidized luciferin emits light on returning to the ground state as indicated in the following reaction:

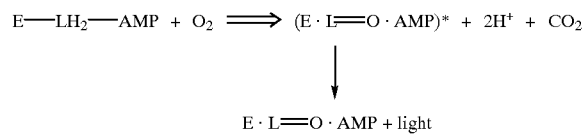

One quantum of light is emitted for each molecule of luciferin oxidized. The electronically excited state of the oxidized luciferin is a characteristic state of the luciferase-luciferin reaction of a beetle luciferase; the color (and, therefore, the energy) of the light emitted upon return of the oxidized luciferin to the ground state is determined by the enzyme, as evidenced by the fact that various species of beetles having the same luciferin emit differently colored light.

Luciferases have been isolated directly from various sources. The cDNAs encoding luciferases of various beetle species have been reported. (See de Wet et al., Molec. Cell. Biol 7, 725–737 (1987); Masuda et al., Gene 77, 265–270 (1989); Wood et al., Science 244, 700–702 (1989)). With the cDNA encoding a beetle luciferase in hand, it is entirely straightforward for the skilled to prepare large amounts of the luciferase by isolation from bacteria (e.g., E. coli), yeast, mammalian cells in culture, or the like, which have been transformed to express the cDNA. Alternatively, the cDNA, under control of an appropriate promoter and other signals for controlling expression, can be used in such a cell to provide luciferase, and ultimately bioluminescence catalyzed thereby, as a signal to indicate activity of the promoter. The activity of the promoter may, in turn, reflect another factor that is sought to be monitored, such as the concentration of a substance that induces or represses the activity of the promoter. Various cell-free systems, that have recently become available to make proteins from nucleic acids encoding them, can also be used to make beetle luciferases.

Further, the availability of cDNAS encoding beetle luciferases and the ability to rapidly screen for CDNAS that encode enzymes which catalyze the luciferase-luciferin reaction (see de Wet et al., supra and Wood et al., supra) also allow the skilled to prepare, and obtain in large amounts, other luciferases that retain activity in catalyzing production of bioluminescence through the luciferase-luciferin reaction. These other luciferases can also be prepared, and the cDNAs that encode them can also be used, as indicated in the previous paragraph. In the present disclosure, the term "beetle luciferase" or "luciferase" means an enzyme that is capable of catalyzing the oxidation of luciferin to yield bioluminescence, as outlined above.

The ready availability of cDNAS encoding beetle luciferases makes possible the use of the luciferases as reporters in assays employed to signal, monitor or measure genetic events associated with transcription and translation, by coupling expression of such a cDNA, and consequently production of the enzyme, to such genetic events.

Firefly luciferase has been widely used to detect promoter activity in eucaryotes. Though this enzyme has also been used in procaryotes, the utility of firefly luciferase as genetic reporter in bacteria is not commonly recognized. As genetic reporters, beetle luciferases are particularly useful since they are monomeric products of a single gene. In addition, no post-translational modifications are required for enzymatic activity, and the enzyme contains no prosthetic groups, bound cofactors, or disulfide bonds. Luminescence from E.coli containing the gene for firefly luciferase can be triggered by adding the substrate luciferin to the growth medium. Luciferin readily penetrates biological membranes and cannot be used as a carbon or nitrogen source by E.coli. The other substrates required for the bioluminescent reaction, oxygen and ATP, are available within living cells. However, measurable variations in luminescence color from luciferases would be needed for systems which utilize two or more different luciferases as reporters (signal geneators).

Clones of different beetle luciferases, particularly of a single genus or species, can be utilized together in bioluminescent reporter systems. Expression in exogenous hosts should differ little between these luciferases because of their close sequence similarity. Thus, in particular, the click beetle luciferases may provide a multiple reporter system that can allow the activity of two or more different promoters to be monitored within a single host, or for different populations of cells to be observed simultaneously. The ability to distinguish each of the luciferases in a mixture, however, is limited by the width of their emissions spectra.

One of the most spectacular examples of luminescence color variation occurs in *Pyrophorus plagiophthalamus*, a large click beetle indigenous to the Caribbean. This beetle has two sets of light organs, a pair on the dorsal surface of the prothorax, and a single organ in a ventral cleft of the abdomen. Four different luciferase clones have been isolated from the ventral organ. The luciferin-luciferase reactions catalyzed by these enzymes produces light that ranges from green to orange.

Spectral data from the luciferase-luciferin reaction catalyzed by these four luciferases show four overlapping peaks of nearly even spacing, emitting green (peak intensity: 546 nanometers), yellow-green (peak intensity: 560 nanometers), yellow (peak intensity: 578 nanometers) and orange (peak intensity: 593 nanometers) light. The respective proteins are named LucPplGR, LucPplYG, LucPplYE and LucPpOR. Though the wavelengths of peak intensity of the light emitted by these luciferases range over nearly 50 nm, there is still considerable overlap among the spectra, even those with peaks at 546 and 593 nm. Increasing the difference in wavelength of peak intensity would thus be useful to obtain greater measurement precision in systems using two or more luciferases.

The amino acid sequences of the four luciferases from the ventral organ are highly similar. Comparisons of the sequences show them to be 95 to 99% identical.

It would be desirable to enhance the utility of beetle luciferases for use in systems using multiple reporters to effect mutations in luciferase-encoding cDNAs to produce mutant luciferases which, in the luciferase-luciferin reaction, produce light with differences between wavelengths of peak intensity that are greater than those available using currently available luciferases.

Beetle luciferases are particularly suited for producing these mutant luciferases since color variation is a direct result of changes in the amino acid sequence.

Mutant luciferases of fireflies of genus Luciola are known in the art. Kajiyama et al., U.S. Pat. Nos. 5,219,737 and 5,229,285.

In using luciferase expression in eukaryotic cells for biosensing, it would be desirable to reduce transport of the luciferase to peroxisomes. Sommer et al., Mol. Biol. Cell 3, 749–759 (1992), have described mutations in the three carboxy-terminal amino acids of P. pyralis luciferase that significantly reduce peroxisome-targeting of the enzyme.

The sequences of cDNAs enoding various beetle luciferases, and the amino acid sequences deduced from the cDNA sequences, are known, as indicated in Table I.

TABLE I

References for cDNA and Amino Acid Sequences or Various Wild-Type Beetle Luceferases

| Luceferase | Reference |
| --- | --- |
| LucPp1GR | K. Wood, Ph.D. Dissertation, University of California, San Diego (1989), see also SEQ ID NO: 1; Wood et al., Science 244, 700–702 (1989) |
| LucPp1YG | K. Wood, Ph.D. Dissertation, University of California, San Diego (1989); Wood et al., Science 244, 700–702 (1989) |
| LucPp1YE | K. Wood, Ph.D. Dissertation, University of California, San Diego (1989); Wood et al., Science 244, 700–702 (1989) |

TABLE I-continued

References for cDNA and Amino Acid Sequences
or Various Wild-Type Beetle Luceferases

| Luceferase | Reference |
| --- | --- |
| LucPp1OR | K. Wood, Ph.D. Dissertation, University of California, San Diego (1989); Wood et al., Science 244, 700–702 (1989) |
| Photinus pyralis | de Wet et al., Mol. Cell. Biol. 7, 725–737 (1987); K. Wood, Ph.D. Dissertation, University of California, San Diego (1989); Wood et al., Science 244, 700–702 (1989) |
| Luciola cruciata | Kajiyama et al., U.S. Pat. No. 5,229,285; Masuda et al., U.S. Pat. No. 4,968,613 |
| Luciola lateralis | Kajiyama et al., U.S. Pat. No. 5,229,285 |
| Luciola mingrelica | Devine et al., Biochim. et Biophys. Acta 1173, 121–132 (1993) |

The CDNA and amino acid sequences of LucPplGR, the green-emitting luciferase of the elaterid beetle *Pyrophorus plagiophthalamus*, are shown in SEQ ID NO:1.

The amino acid sequence of LucPplGR, the green-emitting luciferase of the elaterid beetle *Pyrophorus plagiophthalamus*, is shown in SEQ ID NO:2.

The amino acid and cDNA sequences of LucPplYG, the yellow-green-emitting luciferase of the elaterid beetle *Pyrophorus plagiophthalamus*, are shown in SEQ ID NO:3.

The amino acid sequence of LucPplYG, the yellow-green-emitting luciferase of the elaterid beetle *Pyrophorus plagiophthalamus*, is shown in SEQ ID NO:4.

The amino acid and cDNA sequences of LucPplYE, the yellow-emitting luciferase of the elaterid beetle *Pyrophorus plagiophthalamus*, are shown in SEQ ID NO:5.

The amino acid sequence of LucPplYE, the yellow-emitting luciferase of the elaterid beetle *Pyrophorus plagiophthalamus*, is shown in SEQ ID NO:6.

The cDNA and amino acid sequences of LucPplOR, the orange-emitting luciferase of the elaterid beetle *Pyrophorus plagiophthalamus*, are shown in SEQ ID NO:7.

The amino acid sequence of LucPplOR, the orange-emitting luciferase of the elaterid beetle *Pyrophorus plagiophthalamus*, is shown in SEQ ID NO:8.

The cDNA and amino acid sequences of the luciferase of *Photinus pyralis* are shown in SEQ ID NO:9.

The amino acid sequence of the luciferase of *Photinus pyralis* is shown in SEQ ID NO:10.

The cDNA and amino acid sequences of the luciferase of *Luciola cruciata* are shown in SEQ ID NO:11.

The amino acid sequence of the luciferase the of *Luciola cruciata* is shown in SEQ ID NO:12.

The CDNA and amino acid sequences of the luciferase of *Luciola lateralis* are shown in SEQ ID NO:13.

The amino acid sequence of the luciferase of *Luciola lateralis* is shown in SEQ ID NO:14.

The CDNA and amino acid sequences of the luciferase of *Luciola mingrelica* are shown in SEQ ID NO:15.

The amino acid sequence of the luciferase of *Luciola mingrelica* is shown in SEQ ID NO:16.

SUMMARY OF THE INVENTION

The present invention provides mutant luciferases of beetles and DNAs which encode the mutant luciferases. Preferably, the mutant luciferases produce a light of different color from that of the corresponding wild-type luciferase and preferably this difference in color is such that the wavelength of peak intensity of the luminescence of the mutant differs by at least 1 nm from that of the wild-type enzyme.

The mutant luciferases of the invention differ from the corresponding wild-type enzymes by one or more, but typically fewer than three, amino acid substitutions. The luciferases of the invention may also entail changes in one or more of the three carboxy-terminal amino acids to reduce peroxisome targeting.

In one surprising aspect of the invention, it has been discovered that combining in a single mutant two amino acid substitutions, each of which, by itself, occasions a change in color (shift in wavelength of peak intensity) of bioluminescence, causes the mutant to have a shift in wavelength of peak intensity that is greater than either shift caused by the single amino acid substitutions.

cDNAs encoding the mutant luciferases of the invention may be obtained straightforwardly by any standard, site-directed mutagenesis procedure carried out with a cDNA encoding the corresponding wild-type enzyme or another mutant. The mutant luciferases of the invention can be made by standard procedures for expressing the cDNAs which encode them in prokaryotic or eukaryotic cells.

A fuller appreciation of the invention will be gained upon examination of the following detailed description of the invention.

DETAILED DESCRIPTION OF THE INVENTION

In the following description and examples, process steps are carried out and concentrations are measured at room temperature (about 20° C. to 25° C.) and atmospheric pressure unless otherwise specified.

All amino acids referred to in the specification, except the non-enantiomorphic glycine, are L-amino acids unless specified otherwise. An amino acid may be referred to using the one-letter or three-letter designation, as indicated in the following Table II.

TABLE II

Designations for Amino Acids

| Amino Acid | Three-Letter Designation | One-Letter Designation |
| --- | --- | --- |
| L-alanine | Ala | A |
| L-arginine | Arg | R |
| L-asparagine | Asn | N |
| L-aspartic acid | Asp | D |
| L-cysteine | Cys | C |
| L-glutamic acid | Glu | E |
| L-glutamine | Gln | Q |
| glycine | Gly | G |
| L-histidine | His | H |
| L-isoleucine | Ile | I |
| L-leucine | Leu | L |
| L-lysine | Lys | K |
| L-methionine | Met | M |
| L-phenylalanine | Phe | F |
| L-proline | Pro | P |
| L-serine | Ser | S |
| L-threonine | Thr | T |
| L-tryptophan | Trp | W |
| L-tyrosine | Tyr | Y |
| L-valine | Val | V |

"X" means any one of the twenty amino acids listed in Table II.

Peptide or polypeptide sequences are written and numbered from the initiating methionine, which is numbered "1," to the carboxy-terminal amino acid.

A substitution at a position in a polypeptide is indicated with ([designation for original amino acid]$_{[position\ number]}$ [designation for replacing amino acid]. For example substitution of an alanine at position 100 in a polypeptide with a glutamic acid would be indicated by Ala$_{100}$Glu or A$_{100}$E. Typically, the substitution will be preceded by a designation for the polypeptide in which the substitution occurs. For example, if the substitution A$_{100}$E occurs in an hypothetical protein designated "Luck," the substitution would be indicated as Luck-Ala$_{100}$Glu or Luck-A$_{100}$E. If there is more than one substitution in a polypeptide, the indications of the substitutions are separated by slashes. For example, if the hypothetical protein "Luck" has a substitution of glutamic acid for alanine at position 100 and a substitution of asparagine for lysine at position 150, the polypeptide with the substitutions would be indicated as Luck-Ala$_{100}$Glu/Lys$_{150}$Asn or Luck-A$_{100}$E/K$_{150}$N. To indicate different substitutions at a position in a polypeptide, the designations for the substituting amino acids are separated by commas. For example, if the hypothetical "Luck" has substitutions of glutamic acid, glycine or lysine for alanine at position 100, the designation would be Luck-Ala$_{100}$/Glu,Gly,Lys or Luck-A$_{100}$/E,G,K.

The standard, one-letter codes "A," "C," "G," and "T" are used herein for the nucleotides adenylate, cytidylate, guanylate, and thymidylate, respectively. The skilled will understand that, in DNAs, the nucleotides are 2'-deoxyribonucleotide-5'-phosphates (or, at the 5'-end, triphosphates) while, in RNAs, the nucleotides are ribonucleotide-5'-phosphates (or, at the 5'-end, triphosphates) and uridylate (U) occurs in place of T. "N" means any one of the four nucleotides.

Oligonucleotide or polynucleotide sequences are written from the 5'-end to the 3'-end.

The term "mutant luciferase" is used herein to refer to a luciferase which is not naturally occurring and has an amino acid sequence that differs from those of naturally occurring luciferases.

In one of its aspects, the present invention is a mutant beetle luciferase which produces bioluminescence (i.e., catalyzes the oxidation of luciferin to produce bioluminescence) which has a shift in wavelength of peak intensity of at least 1 nm from the wavelength of peak intensity of the bioluminescence produced by the corresponding wild-type luciferase and has an amino acid sequence that differs from that of the corresponding wild-type luciferase by a substitution at one position or substitutions at two positions; provided that, if there is a substitution at one position, the position corresponds to a position in the amino acid sequence of LucPplGR selected from the group consisting of position 214, 215, 223, 224, 232, 236, 237, 238, 242, 244, 245, 247, 248, 282, 283 and 348; provided further that, if there are substitutions at two positions, at least one of the positions corresponds to a position in the amino acid sequence of LucPplGR selected from the group consisting of position 214, 215, 223, 224, 232, 236, 237, 238, 242, 244, 245, 247, 248, 282, 283 and 348; and provided that the mutant optionally has a peroxisome-targeting-avoiding sequence at its carboxy-terminus.

Exemplary mutant luciferases of the invention are those of the group consisting of LucPplGR-R$_{215}$H, -R$_{215}$G, -R$_{215}$T, -R$_{215}$M, -R$_{215}$P, -R$_{215}$A, -R$_{215}$L, -R$_{215}$L, -R$_{223}$L, -R$_{223}$Q, -R$_{223}$M, -R$_{223}$H, -V$_{224}$I, -V$_{224}$S, -V$_{224}$F, -V$_{224}$Y, -V$_{224}$L, -V$_{224}$H, -V$_{224}$G, -V$_{232}$E, -V$_{236}$H, -V$_{236}$W, -Y$_{237}$S, -Y$_{237}$C, -L$_{238}$R, -L$_{238}$M, -L$_{238}$Q, -L$_{238}$S, -L$_{238}$D, -H$_{242}$A, -F$_{244}$L, -G$_{245}$S, -G$_{245}$E, -S$_{247}$H, -S$_{247}$T, -S$_{247}$Y, -S$_{247}$F, -I$_{248}$R, -I$_{248}$V, -I$_{248}$F, -I$_{248}$T, -I$_{248}$S, -I$_{248}$N, -H$_{348}$N, -H$_{348}$Q, -H$_{348}$E, -H$_{348}$C, -S$_{247}$F/F$_{246}$L, -S$_{247}$F/I$_{248}$T, -V$_{224}$F/R$_{215}$G, -V$_{224}$F/R$_{215}$T, -V$_{224}$F/R$_{215}$V, -V$_{224}$F/R$_{215}$P, -V$_{224}$F/P$_{222}$S, -V$_{224}$F/Q$_{227}$E, -V$_{224}$F/L$_{238}$V, -V$_{224}$F/L$_{238}$T, -V$_{224}$F/S$_{247}$G, -V$_{224}$F/S$_{247}$H, -V$_{224}$F/S$_{247}$T, and -V$_{224}$F/S$_{247}$F.

The following Table III shows spectral properties of these and other exemplary mutant luciferases.

TABLE III

| Protein | Spectral Properties | | |
|---|---|---|---|
| LUCPp1GR- | peak | shift | width |
| w.t. | 545 | 0 | 72 |
| V$_{214}$S | * | | |
| Q | * | | |
| Y | * | | |
| K | * | | |
| L | * | | |
| G | * | | |
| C | * | | |
| E | * | | |
| F | * | | |
| P | * | | |
| H | * | | |
| R | * | | |
| R$_{215}$H | 562 | 17 | 82 |
| Q | 567 | 22 | 81 |
| G | 576 | 31 | 82 |
| T | 576 | 31 | 84 |
| M | 582 | 37 | 83 |
| P | 588 | 43 | 91 |
| S | * | | |
| Y | * | | |
| K | * | | |
| L | * | | |
| C | * | | |
| E | * | | |
| F | * | | |
| R$_{223}$L | 549 | 4 | 75 |
| Q | 549 | 4 | 73 |
| R$_{223}$M | 549 | 4 | 75 |
| H | 551 | 6 | 75 |
| S | * | | |
| Y | * | | |
| K | * | | |
| G | * | | |
| C | * | | |
| E | * | | |
| F | * | | |
| P | * | | |
| V$_{224}$I | 546 | 1 | 75 |
| S | 556 | 11 | 70 |
| F | 561 | 16 | 84 |
| Y | 565 | 20 | 87 |
| L | 578 | 33 | 94 |
| H | 584 | 39 | 69 |
| G | 584 | 39 | 70 |
| V$_{232}$E | 554 | 9 | 83 |
| V$_{236}$H | 554 | 9 | 74 |
| W | 554 | 9 | 74 |
| Y$_{237}$S | 553 | 8 | 73 |
| C | 554 | 9 | 74 |
| L$_{238}$R | 544 | −1 | 72 |
| M | 555 | 10 | 75 |
| Q | 557 | 12 | 76 |
| S | 559 | 14 | 73 |
| D | 568 | 23 | 76 |
| H$_{242}$A | 559 | 14 | 75 |
| H$_{242}$S | 561 | 16 | 74 |
| F$_{244}$L | 555 | 10 | 73 |
| G$_{245}$S | 558 | 13 | 75 |
| E | 574 | 29 | 79 |
| S$_{247}$H | 564 | 19 | 72 |
| Y | 566 | 21 | 79 |
| F | 569 | 24 | 84 |
| I$_{248}$R | 544 | −1 | 72 |
| V | 546 | 1 | 72 |
| F | 548 | 3 | 74 |

TABLE III-continued

| Protein | Spectral Properties | | |
|---|---|---|---|
| LUCPp1GR- | peak | shift | width |
| T | 554 | 9 | 75 |
| S | 558 | 13 | 80 |
| N | 577 | 32 | 90 |
| $H_{348}A$ | 592 | 47 | 67 |
| C | 593 | 48 | 66 |
| N | 597 | 52 | 67 |
| Q | 605 | 60 | 72 |
| $V_{214}C/Y_{224}A$ | 559 | 14 | 72 |
| $S_{247}F/F_{246}L$ | 567 | 22 | 79 |
| $S_{247}F/I_{248}C$ | 586 | 41 | 84 |
| $S_{247}F/I_{248}T$ | 596 | 51 | 80 |
| $T_{233}A/L_{238}M$ | 555 | 10 | 75 |
| $V_{282}I/I_{283}V$ | 563 | 3 | 73 |
| $V_{224}F/R_{215}G$ | 584 | 39 | 80 |
| $V_{224}F/R_{215}T$ | 587 | 42 | 80 |
| $V_{224}F/R_{215}V$ | 589 | 44 | 80 |
| $V_{224}F/R_{215}P$ | 597 | 52 | 81 |
| $V_{224}F/P_{222}S$ | 564 | 3 | 86 |
| $V_{224}F/Q_{227}E$ | 583 | 38 | 85 |
| $V_{224}F/L_{238}V$ | 575 | 30 | 85 |
| $V_{224}F/L_{238}M$ | 576 | 31 | 87 |
| $V_{224}F/S_{247}G$ | 581 | 36 | 84 |
| $V_{224}F/S_{247}H$ | 581 | 36 | 79 |
| $V_{224}F/S_{247}Y$ | 595 | 50 | 88 |
| $V_{224}F/S_{247}F$ | 597 | 52 | 85 |

*Spectral shift ($\geq 2$ nm) observed by eye.

"Corresponding positions" in luciferases other than LucPp1GR can be determined either from alignments at the amino acid level that are already known in the art (see, e.g., Wood et al., Science 244, 700–702 (1989); Devine et al., Biochim. et Biophys. Acta 1173, 121–132(1993)) or by simply aligning at the amino acid level to maximize alignment of identical or conservatively substituted residues, and keeping in mind in particular that amino acids 195–205 in the LucPp1GR sequence are very highly conserved in all beetle luciferases and that there are no gaps for more than 300 positions after that highly conserved 11-mer in any beetle luciferase aminio acid sequence.

A "peroxisome-targeting-avoiding sequence at its carboxy-terminus" means (1) the three carboxy-terminal amino acids of the corresponding wild-type luciferase are entirely missing from the mutant; or (2) the three carboxy-terminal amino acids of the corresponding wild-type luciferase are replaced with a sequence, of one, two or three amino acids that, in accordance with Sommer et al., supra, will reduce peroxisome-targeting by at least 50%. If the three carboxy-terminal amino acids of the wild-type luciferase are replaced by a three-amino-acid peroxisome-targeting-avoiding sequence in the mutant, and if the sequence in the mutant is $X_1X_2X_3$, where $X_3$ is carboxy-terminal, than $X_1$ is any of the twenty amino acids except A, C, G, H, N, P, Q, T and S, $X_2$ is any of the twenty amino acids except H, M, N, Q, R, S and K, and $X_3$ is any of the twenty amino acids except I, M, Y and L. Further, any one or two, or all three, of $X_1$, $X_2$, and $X_3$ could be absent from the mutant (i.e., no amino acid corresponding to the position). The most preferred peroxisome-targeting-avoiding sequence is IAV, where V is at the carboxy-terminus.

In another of its aspects, the invention entails a combination of luciferases, in a cell (eukaryotic or prokaryotic), a solution (free or linked as a reporter to an antibody, antibody-fragment, nucleic acid probe, or the like), or adhered to a solid surface, optionally through an antibody, antibody fragment or nucleic acid, and exposed to a solution, provided that at least one of the luciferases is a mutant, both of the luciferases remain active in producing bioluminescence, and the wavelengths of peak intensities of the bioluminescence of the luciferases differ because the amino acid sequences of the luciferases differ at at least one of the positions corresponding to positions 214, 215, 223, 224, 232, 236, 237, 238, 242, 244, 245, 247, 248, 282, 283 and 348 in the amino acid sequence of LucPp1GR, provided that one or both of the luciferases optionally have peroxisome-targeting-avoiding sequences.

In another of its aspects, the invention entails a DNA molecule, which may be an eukaryotic or prokaryotic expression vector, which comprises a segment which has a sequence which encodes a mutant beetle luciferase of the invention.

Most preferred among the DNAs of the invention are those with segments which encode a preferred mutant luciferase of the invention.

From the description of the invention provided herein, the skilled will recognize many modifications and variations of what has been described that are within the spirit of the invention. It is intended that such modifications and variations also be understood as part of the invetion.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 1632 base pairs
      (B) TYPE: nucleic acid
      (C) STRANDEDNESS: double
      (D) TOPOLOGY: linear (ii) MOLECULE TYPE: cDNA to mRNA1

(iii) HYPOTHETICAL: no (iv) ANTI-SENSE: no

-continued (xi) SEQUENCE DESCRIPTION: SEQ ID NO:1:

```
ATG ATG AAG AGA GAG AAA AAT GTT GTA TAT GGA CCC GAA CCC CTA CAC        48
Met Met Lys Arg Glu Lys Asn Val Val Tyr Gly Pro Glu Pro Leu His
              5                  10                  15

CCC TTG GAA GAC TTA ACA GCA GGA GAA ATG CTC TTC AGG GCC CTT CGA        96
Pro Leu Glu Asp Leu Thr Ala Gly Glu Met Leu Phe Arg Ala Leu Arg
             20                  25                  30

AAA CAT TCT CAT TTA CCG CAG GCT TTA GTA GAT GTG TAT GGT GAA GAA       144
Lys His Ser His Leu Pro Gln Ala Leu Val Asp Val Tyr Gly Glu Glu
             35                  40                  45

TGG ATT TCA TAT AAA GAG TTT TTT GAA ACT ACA TGC CTA CTA GCA CAA       192
Trp Ile Ser Tyr Lys Glu Phe Phe Glu Thr Thr Cys Leu Leu Ala Gln
         50                  55                  60

AGT CTT CAC AAT TGT GGA TAC AAG ATG AGT GAT GTA GTG TCG ATC TGC       240
Ser Leu His Asn Cys Gly Tyr Lys Met Ser Asp Val Val Ser Ile Cys
65                  70                  75                  80

GCG GAG AAC AAT AAA AGA TTT TTT GTT CCC ATT ATT GCA GCT TGG TAT       288
Ala Glu Asn Asn Lys Arg Phe Phe Val Pro Ile Ile Ala Ala Trp Tyr
                 85                  90                  95

ATT GGT ATG ATT GTA GCA CCT GTT AAT GAG GGC TAC ATC CCA GAT GAA       336
Ile Gly Met Ile Val Ala Pro Val Asn Glu Gly Tyr Ile Pro Asp Glu
            100                 105                 110

CTC TGT AAG GTC ATG GGT ATA TCG AGA CCA CAA CTA GTT TTT TGT ACA       384
Leu Cys Lys Val Met Gly Ile Ser Arg Pro Gln Leu Val Phe Cys Thr
        115                 120                 125

AAG AAT ATT CTA AAT AAG GTA TTG GAG GTA CAG AGC AGA ACT GAT TTC       432
Lys Asn Ile Leu Asn Lys Val Leu Glu Val Gln Ser Arg Thr Asp Phe
    130                 135                 140

ATA AAA AGG ATT ATC ATA CTA GAT GCT GTA GAA AAC ATA CAC GGT TGT       480
Ile Lys Arg Ile Ile Ile Leu Asp Ala Val Glu Asn Ile His Gly Cys
145                 150                 155                 160

GAA AGT CTT CCC AAT TTT ATT TCT CGT TAT TCG GAT GGA AAT ATT GCC       528
Glu Ser Leu Pro Asn Phe Ile Ser Arg Tyr Ser Asp Gly Asn Ile Ala
                165                 170                 175

AAC TTC AAA CCT TTA CAT TAC GAT CCT GTT GAA CAA GTG GCA GCT ATC       576
Asn Phe Lys Pro Leu His Tyr Asp Pro Val Glu Gln Val Ala Ala Ile
            180                 185                 190

TTA TGT TCG TCA GGC ACA ACT GGA TTA CCG AAA GGT GTA ATG CAA ACT       624
Leu Cys Ser Ser Gly Thr Thr Gly Leu Pro Lys Gly Val Met Gln Thr
        195                 200                 205

CAT AGA AAT GTT TGT GTC CGA CTT ATA CAT GCT TTA GAC CCC AGG GTA       672
His Arg Asn Val Cys Val Arg Leu Ile His Ala Leu Asp Pro Arg Val
    210                 215                 220

GGA ACG CAA CTT ATT CCT GGT GTG ACA GTC TTA GTA TAT CTG CCT TTT       720
Gly Thr Gln Leu Ile Pro Gly Val Thr Val Leu Val Tyr Leu Pro Phe
225                 230                 235                 240

TTC CAT GCT TTT GGG TTC TCT ATA AAC TTG GGA TAC TTC ATG GTG GGT       768
Phe His Ala Phe Gly Phe Ser Ile Asn Leu Gly Tyr Phe Met Val Gly
                245                 250                 255

CTT CGT GTT ATC ATG TTA AGA CGA TTT GAT CAA GAA GCA TTT CTA AAA       816
Leu Arg Val Ile Met Leu Arg Arg Phe Asp Gln Glu Ala Phe Leu Lys
            260                 265                 270

GCT ATT CAG GAT TAT GAA GTT CGA AGT GTA ATT AAC GTT CCA GCA ATA       864
Ala Ile Gln Asp Tyr Glu Val Arg Ser Val Ile Asn Val Pro Ala Ile
        275                 280                 285

ATA TTG TTC TTA TCG AAA AGT CCT TTG GTT GAC AAA TAC GAT TTA TCA       912
Ile Leu Phe Leu Ser Lys Ser Pro Leu Val Asp Lys Tyr Asp Leu Ser
    290                 295                 300
```

-continued

```
AGT TTA AGG GAA TTG TGT TGC GGT GCG GCA CCA TTA GCA AAG GAA GTT    960
Ser Leu Arg Glu Leu Cys Cys Gly Ala Ala Pro Leu Ala Lys Glu Val
305                 310                 315                 320

GCT GAG ATT GCA GTA AAA CGA TTA AAC TTG CCA GGA ATT CGC TGT GGA   1008
Ala Glu Ile Ala Val Lys Arg Leu Asn Leu Pro Gly Ile Arg Cys Gly
                325                 330                 335

TTT GGT TTG ACA GAA TCT ACT TCA GCT AAT ATA CAC AGT CTT AGG GAT   1056
Phe Gly Leu Thr Glu Ser Thr Ser Ala Asn Ile His Ser Leu Arg Asp
                340                 345                 350

GAA TTT AAA TCA GGA TCA CTT GGA AGA GTT ACT CCT TTA ATG GCA GCT   1104
Glu Phe Lys Ser Gly Ser Leu Gly Arg Val Thr Pro Leu Met Ala Ala
                355                 360                 365

AAA ATA GCA GAT AGG GAA ACT GGT AAA GCA TTG GGA CCA AAT CAA GTT   1152
Lys Ile Ala Asp Arg Glu Thr Gly Lys Ala Leu Gly Pro Asn Gln Val
        370                 375                 380

GGT GAA TTA TGC ATT AAA GGT CCC ATG GTA TCG AAA GGT TAC GTG AAC   1200
Gly Glu Leu Cys Ile Lys Gly Pro Met Val Ser Lys Gly Tyr Val Asn
385                 390                 395                 400

AAT GTA GAA GCT ACC AAA GAA GCT ATT GAT GAT GAT GGT TGG CTT CAC   1248
Asn Val Glu Ala Thr Lys Glu Ala Ile Asp Asp Asp Gly Trp Leu His
                405                 410                 415

TCT GGA GAC TTT GGA TAC TAT GAT GAG GAT GAG CAT TTC TAT GTG GTG   1296
Ser Gly Asp Phe Gly Tyr Tyr Asp Glu Asp Glu His Phe Tyr Val Val
                420                 425                 430

GAC CGT TAC AAG GAA TTG ATT AAA TAT AAG GGC TCT CAG GTA GCA CCT   1344
Asp Arg Tyr Lys Glu Leu Ile Lys Tyr Lys Gly Ser Gln Val Ala Pro
                435                 440                 445

GCA GAA CTA GAA GAG ATT TTA TTG AAA AAT CCA TGT ATC AGA GAT GTT   1392
Ala Glu Leu Glu Glu Ile Leu Leu Lys Asn Pro Cys Ile Arg Asp Val
        450                 455                 460

GCT GTG GTT GGT ATT CCT GAT CTA GAA GCT GGA GAA CTG CCA TCT GCG   1440
Ala Val Val Gly Ile Pro Asp Leu Glu Ala Gly Glu Leu Pro Ser Ala
465                 470                 475                 480

TTT GTG GTT ATA CAG CCC GGA AAG GAG ATT ACA GCT AAA GAA GTT TAC   1488
Phe Val Val Ile Gln Pro Gly Lys Glu Ile Thr Ala Lys Glu Val Tyr
                485                 490                 495

GAT TAT CTT GCC GAG AGG GTC TCC CAT ACA AAG TAT TTG CGT GGA GGG   1536
Asp Tyr Leu Ala Glu Arg Val Ser His Thr Lys Tyr Leu Arg Gly Gly
                500                 505                 510

GTT CGA TTC GTT GAT AGC ATA CCA AGG AAT GTT ACA GGT AAA ATT ACA   1584
Val Arg Phe Val Asp Ser Ile Pro Arg Asn Val Thr Gly Lys Ile Thr
                515                 520                 525

AGA AAG GAA CTT CTG AAG CAG TTG CTG GAG AAG AGT TCT AAA CTT TAA   1632
Arg Lys Glu Leu Leu Lys Gln Leu Leu Glu Lys Ser Ser Lys Leu
                530                 535                 540
```

What is claimed is:

1. An isolated DNA molecule comprising a segment having a sequence which encodes a synthetic mutant beetle luciferase comprising an amino acid sequence that differs from that of the corresponding wild-type luciferase by at least one amino acid substitution, the position of the amino acid substitution corresponding to a position in the amino acid sequence of LucPplGR of SEQ ID NO:2 selected from the group consisting of position 215, 224, 232, 236, 237, 242, 244, 245, 248, 282, 283 and 348, wherein the mutant luciferase produces bioluminescence having a shift in wavelength of peak intensity of at least 1 nanometer relative to the bioluminescence produced by the wild-type luciferase.

2. An isolated DNA molecule according to claim 1, wherein the encoded mutant luciferase has one amino acid substitution.

3. An isolated DNA molecule according to claim 1, wherein the encoded mutant luciferase has two amino acid substitutions.

4. An isolated DNA molecule according to claim 3 wherein, in the encoded mutant luciferase, each of the amino acid substitutions is at a position corresponding to a position in the amino acid sequence of LucPplGR of SEQ ID NO:2 selected from the group consisting of position 215, 224, 232, 236, 237, 242, 244, 245, 248, 282, 283 and 348.

5. An isolated DNA molecule according to claim 1 wherein, for the encoded amino acid sequence, the corresponding wild-type luciferase is selected from the group consisting of LucPplGR of SEQ ID NO:2, LucPplYG of SEQ ID NO:4, LucPplYE of SEQ ID NO:6, LucPplOR of SEQ ID NO:8, the luciferase of *Photinus pyralis* of SEQ ID NO:10, the luciferase of *Luciola cruciata* of SEQ ID NO:12, the luciferase of *Luciola lateralis* of SEQ ID NO:14, and the luciferase of *Luciola mingrelica* of SEQ ID NO:16.

6. An isolated DNA molecule according to claim 2 wherein, for the encoded amino acid sequence, the corresponding wild-type luciferase is selected from the group consisting of LucPplGR of SEQ ID NO:2, LucPplYG of SEQ ID NO:4, LucPplYE of SEQ ID NO:6, LucPplOR of SEQ ID NO:8, the luciferase of *Photinus pyralis* of SEQ ID NO:10, the luciferase of *Luciola cruciata* of SEQ ID NO:12, the luciferase of *Luciola lateralis* of SEQ ID NO:14, and the luciferase of *Luciola mingrelica* of SEQ ID NO:16.

7. An isolated DNA molecule according to claim 3 wherein, for the encoded amino acid sequence, the corresponding wild-type luciferase is selected from the group consisting of LucPplGR of SEQ ID NO:2, LucPplYG of SEQ ID NO:4, LucPplYE of SEQ ID NO:6, LucPplOR of SEQ ID NO:8, the luciferase of *Photinus pyralis* of SEQ ID NO:10, the luciferase of *Luciola cruciata* of SEQ ID NO:12, the luciferase of *Luciola lateralis* of SEQ ID NO:14, and the luciferase of *Luciola mingrelica* of SEQ ID NO:16.

8. An isolated DNA molecule according to claim 4 wherein, for the encoded amino acid sequence, the corresponding wild-type luciferase is selected from the group consisting of LucPplGR of SEQ ID NO:2, LucPplYG of SEQ ID NO:4, LucPplYE of SEQ ID NO:6, LucPplOR of SEQ ID NO:8, the luciferase of Photinus pyralis of SEQ ID NO:10, the luciferase of *Luciola cruciata* of SEQ ID NO:12, the luciferase of *Luciola lateralis* of SEQ ID NO:14, and the luciferase of Luciola mingrelica of SEQ ID NO:16.

9. An isolated DNA molecule according to claim 5 wherein, for the encoded amino acid sequence, the corresponding wild-type luciferase is selected from the group consisting of LucPplGR of SEQ ID NO:2, LucPplYG of SEQ ID NO:4, LucPplYE of SEQ ID NO:6, and LucPplOR of SEQ ID NO:8.

10. An isolated DNA molecule according to claim 6 wherein, for the encoded amino acid sequence, the corresponding wild-type luciferase is selected from the group consisting of LucPplGR of SEQ ID NO:2, LucPplYG of SEQ ID NO:4, LucPplYE of SEQ ID NO:6, LucPplOR of SEQ ID NO:8.

11. An isolated DNA molecule according to claim 7 wherein, for the encoded amino acid sequence, the corresponding wild-type luciferase is selected from the group consisting of LucPplGR of SEQ ID NO:2, LucPplYG of SEQ ID NO:4, LucPplYE of SEQ ID NO:6, and LucPplOR of SEQ ID NO:8.

12. An isolated DNA molecule according to claim 8 wherein, for the encoded amino acid sequence, the corresponding wild-type luciferase is selected from the group consisting of LucPplGR of SEQ ID NO:2, LucPplYG of SEQ ID NO:4, LucPplYE of SEQ ID NO:6, LucPplOR of SEQ ID NO:8.

13. An isolated DNA molecule according to claim 9 wherein, for the encoded amino acid sequence, the corresponding wild-type luciferase is LucPplGR of SEQ ID NO:2.

14. An isolated DNA molecule according to claim 10 wherein, for the encoded amino acid sequence, the corresponding wild-type luciferase is LucPplGR of SEQ ID NO:2.

15. An isolated DNA molecule according to claim 11 wherein, for the encoded amino acid sequence, the corresponding wild-type luciferase is LucPplGR of SEQ ID NO:2.

16. An isolated DNA molecule according to claim 12 wherein, for the encoded amino acid sequence, the corresponding wild-type luciferase is LucPplGR of SEQ ID NO:2.

17. An isolated DNA molecule according to claim 13 wherein the encoded synthetic mutant luciferase is selected from the group consisting of LucPplGR -$R_{215}H$, -$R_{215}G$, -$R_{215}T$, -$R_{215}M$, -$R_{215}P$, -$R_{215}A$, -$R_{215}L$, -$V_{224}I$, -$V_{224}S$, -$V_{224}F$, -$V_{224}Y$, -$V_{224}L$, -$V_{224}H$, -$V_{224}G$, -$V_{232}E$, -$V_{236}H$, -$V_{236}W$, -$Y_{237}S$, -$Y_{237}C$, -$H_{242}A$, -$F_{244}L$, -$G_{245}S$, -$G_{245}E$, -$I_{248}R$, -$I_{248}V$, -$I_{248}F$, -$I_{248}T$, -$S_{247}F/I_{248}T$, -$V_{224}F/R_{215}G$, -$V_{224}F/R_{215}T$, -$V_{224}F/R_{215}V$, -$V_{227}F/R_{215}P$, -$V_{224}F/P_{222}S$, -$V_{224}F/Q_{227}E$, -$V_{224}F/L_{238}V$, -$V_{224}F/L_{238}T$, -$V_{224}F/S_{247}G$ -$V_{224}F/S_{247}H$, -$V_{224}F/S_{247}T$, and -$V_{224}F/S_{247}F$.

18. An isolated DNA molecule according to claim 1, wherein the position of the amino acid substitution corresponds to position 215 in the amino acid sequence of LucPplGR of SEQ ID NO:2.

19. An isolated DNA molecule according to claim 1, wherein the position of the amino acid substitution corresponds to position 224 in the amino acid sequence of LucPplGR of SEQ ID NO:2.

20. An isolated DNA molecule according to claim 1, wherein the position of the amino acid substitution corresponds to position 232 in the amino acid sequence of LucPplGR of SEQ ID NO:2.

21. An isolated DNA molecule according to claim 1, wherein the position of the amino acid substitution corresponds to position 236 in the amino acid sequence of LucPplGR of SEQ ID NO:2.

22. An isolated DNA molecule according to claim 1, wherein the position of the amino acid substitution corresponds to position 237 in the amino acid sequence of LucPplGR of SEQ ID NO:2.

23. An isolated DNA molecule according to claim 1, wherein the position of the amino acid substitution corresponds to position 242 in the amino acid sequence of LucPplGR of SEQ ID NO:2.

24. An isolated DNA molecule according to claim 1, wherein the position of the amino acid substitution corresponds to position 244 in the amino acid sequence of LucPplGR of SEQ ID NO:2.

25. An isolated DNA molecule according to claim 1, wherein the position of the amino acid substitution corresponds to position 245 in the amino acid sequence of LucPplGR of SEQ ID NO:2.

26. An isolated DNA molecule according to claim 1, wherein the position of the amino acid substitution corresponds to position 248 in the amino acid sequence of LucPplGR of SEQ ID NO:2.

27. An isolated DNA molecule comprising a segment having a sequence which encodes a synthetic mutant beetle luciferase having an amino acid sequence that differs from that of the corresponding wild-type luciferase by at least one amino acid substitution, the position of the amino acid substitution corresponding to position 282 in the amino acid sequence of LucPplGR of SEQ ID NO:2, wherein the mutant luciferase produces bioluminescence having a shift in wavelength of peak intensity of at least 1 nanometer relative to the bioluminescence produced by the wild-type luciferase.

28. An isolated DNA molecule comprising a segment having a sequence which encodes a synthetic mutant beetle luciferase having an amino acid sequence that differs from that of the corresponding wild-type luciferase by at least one amino acid substitution, the position of the amino acid substitution corresponding to position 283 in the amino acid sequence of LucPplGR of SEQ ID NO:2, wherein the mutant luciferase produces bioluminescence having a shift in wavelength of peak intensity of at least 1 nanometer relative to the bioluminescence produced by the wild-type luciferase.

29. An isolated DNA molecule according to claim 1, wherein the position of the amino acid substitution corresponds to position 348 in the amino acid sequence of LucPplGR of SEQ ID NO:2.

30. An isolated DNA molecule comprising a segment having a sequence which encodes a mutant beetle luciferase having an amino acid sequence that differs from that of the corresponding wild-type luciferase LucPplGR by at least one amino acid substitution, wherein the encoded mutant luciferase is selected from the group consisting of LucPplGR-$_{223}$L, -R$_{223}$Q, -R$_{223}$M, -R$_{223}$H, -L$_{238}$R, -L$_{238}$M, -L$_{238}$Q, -L$_{238}$S, -S$_{247}$H, -S$_{247}$T, -S$_{247}$Y -S$_{247}$F and the encoded mutant luciferase produces bioluminescence having a shift in wavelength of peak intensity of at least 1 nanometer relative to the bioluminescence produced by the wild-type luciferase.

* * * * *

UNITED STATES PATENT AND TRADEMARK OFFICE
CERTIFICATE OF CORRECTION

| | | |
|---|---|---|
| PATENT NO. | : 6,552,179 B1 | Page 1 of 52 |
| APPLICATION NO. | : 08/478205 | |
| DATED | : April 22, 2003 | |
| INVENTOR(S) | : Keith V. Wood and Monika G. Wood | |

It is certified that error appears in the above-identified patent and that said Letters Patent is hereby corrected as shown below:

In column 13, after the end of SEQ ID NO:1, insert

-- (2) INFORMATION FOR SEQ ID NO:2:

(i) SEQUENCE CHARACTERISTICS:

(A) LENGTH: 543 amino acids
      (B) TYPE: amino acid
      (D) TOPOLOGY: linear (ii) MOLECULE TYPE: protein (xi) SEQUENCE DESCRIPTION: SEQ ID NO:2:

```
Met Met Lys Arg Glu Lys Asn Val Val Tyr G ly Pro Glu Pro Leu His
 1               5                  10                  15

Pro Leu Glu Asp Leu Thr Ala Gly Glu Met L eu Phe Arg Ala Leu Arg
                20                  25                  30

Lys His Ser His Leu Pro Gln Ala Leu Val A sp Val Tyr Gly Glu Glu
            35                  40                  45

Trp Ile Ser Tyr Lys Glu Phe Phe Glu Thr T hr Cys Leu Leu Ala Gln
        50                  55                  60

Ser Leu His Asn Cys Gly Tyr Lys Met Ser A sp Val Val Ser Ile Cys
65                  70                  75                  80

Ala Glu Asn Asn Lys Arg Phe Phe Val Pro I le Ile Ala Ala Trp Tyr
                85                  90                  95

Ile Gly Met Ile Val Ala Pro Val Asn Glu G ly Tyr Ile Pro Asp Glu
               100                 105                 110

Leu Cys Lys Val Met Gly Ile Ser Arg Pro G ln Leu Val Phe Cys Thr
               115                 120                 125

Lys Asn Ile Leu Asn Lys Val Leu Glu Val G ln Ser Arg Thr Asp Phe
           130                 135                 140
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Ile Lys Arg Ile Ile Ile Leu Asp Ala Val G lu Asn Ile His Gly Cys
145                 150             155                 160

Glu Ser Leu Pro Asn Phe Ile Ser Arg Tyr S er Asp Gly Asn Ile Ala
                165             170                 175

Asn Phe Lys Pro Leu His Tyr Asp Pro Val G lu Gln Val Ala Ala Ile
            180             185                 190

Leu Cys Ser Ser Gly Thr Thr Gly Leu Pro L ys Gly Val Met Gln Thr
            195             200                 205

His Arg Asn Val Cys Val Arg Leu Ile His A la Leu Asp Pro Arg Val
        210             215             220

Gly Thr Gln Leu Ile Pro Gly Val Thr Val L eu Val Tyr Leu Pro Phe
225             230                 235                 240

Phe His Ala Phe Gly Phe Ser Ile Asn Leu G ly Tyr Phe Met Val Gly
                245             250                 255

Leu Arg Val Ile Met Leu Arg Arg Phe Asp G ln Glu Ala Phe Leu Lys
                260             265                 270

Ala Ile Gln Asp Tyr Glu Val Arg Ser Val I le Asn Val Pro Ala Ile
            275             280                 285

Ile Leu Phe Leu Ser Lys Ser Pro Leu Val A sp Lys Tyr Asp Leu Ser
        290             295             300

Ser Leu Arg Glu Leu Cys Cys Gly Ala Ala P ro Leu Ala Lys Glu Val
305             310             315                 320

Ala Glu Ile Ala Val Lys Arg Leu Asn Leu P ro Gly Ile Arg Cys Gly
            325             330                 335

Phe Gly Leu Thr Glu Ser Thr Ser Ala Asn I le His Ser Leu Arg Asp
            340             345                 350
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Ile Lys Arg Ile Ile Ile Leu Asp Ala Val G lu Asn Ile His Gly Cys
145                 150                 155                 160

Glu Ser Leu Pro Asn Phe Ile Ser Arg Tyr S er Asp Gly Asn Ile Ala
                165                 170                 175

Asn Phe Lys Pro Leu His Tyr Asp Pro Val G lu Gln Val Ala Ala Ile
            180                 185                 190

Leu Cys Ser Ser Gly Thr Thr Gly Leu Pro L ys Gly Val Met Gln Thr
                195             200                 205

His Arg Asn Val Cys Val Arg Leu Ile His A la Leu Asp Pro Arg Val
            210                 215                 220

Gly Thr Gln Leu Ile Pro Gly Val Thr Val L eu Val Tyr Leu Pro Phe
225                 230                 235                 240

Phe His Ala Phe Gly Phe Ser Ile Asn Leu G ly Tyr Phe Met Val Gly
                245                 250                 255

Leu Arg Val Ile Met Leu Arg Arg Phe Asp G ln Glu Ala Phe Leu Lys
            260                 265                 270

Ala Ile Gln Asp Tyr Glu Val Arg Ser Val I le Asn Val Pro Ala Ile
            275                 280                 285

Ile Leu Phe Leu Ser Lys Ser Pro Leu Val A sp Lys Tyr Asp Leu Ser
        290                 295                 300

Ser Leu Arg Glu Leu Cys Cys Gly Ala Ala P ro Leu Ala Lys Glu Val
305                 310                 315                 320

Ala Glu Ile Ala Val Lys Arg Leu Asn Leu P ro Gly Ile Arg Cys Gly
                325                 330                 335

Phe Gly Leu Thr Glu Ser Thr Ser Ala Asn I le His Ser Leu Arg Asp
            340                 345                 350
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Glu Phe Lys Ser Gly Ser Leu Gly Arg Val Thr Pro Leu Met Ala Ala
            355                 360                 365
Lys Ile Ala Asp Arg Glu Thr Gly Lys Ala Leu Gly Pro Asn Gln Val
        370                 375                 380
Gly Glu Leu Cys Ile Lys Gly Pro Met Val Ser Lys Gly Tyr Val Asn
385                 390                 395                 400
Asn Val Glu Ala Thr Lys Glu Ala Ile Asp Asp Asp Gly Trp Leu His
                405                 410                 415
Ser Gly Asp Phe Gly Tyr Tyr Asp Glu Asp Glu His Phe Tyr Val Val
            420                 425                 430
Asp Arg Tyr Lys Glu Leu Ile Lys Tyr Lys Gly Ser Gln Val Ala Pro
        435                 440                 445
Ala Glu Leu Glu Glu Ile Leu Leu Lys Asn Pro Cys Ile Arg Asp Val
    450                 455                 460
Ala Val Val Gly Ile Pro Asp Leu Glu Ala Gly Glu Leu Pro Ser Ala
465                 470                 475                 480
Phe Val Val Ile Gln Pro Gly Lys Glu Ile Thr Ala Lys Glu Val Tyr
                485                 490                 495
Asp Tyr Leu Ala Glu Arg Val Ser His Thr Lys Tyr Leu Arg Gly Gly
            500                 505                 510
Val Arg Phe Val Asp Ser Ile Pro Arg Asn Val Thr Gly Lys Ile Thr
        515                 520                 525
Arg Lys Glu Leu Leu Lys Gln Leu Leu Glu Lys Ser Ser Lys Leu
    530                 535                 540

(2) INFORMATION FOR SEQ ID NO:3:

(i) SEQUENCE CHARACTERISTICS:
        (A) LENGTH: 1770 base pairs
        (B) TYPE: nucleic acid
        (C) STRANDEDNESS: single
        (D) TOPOLOGY: linear
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
    (ix) FEATURE:
         (A) NAME/KEY: CDS
         (B) LOCATION: 36..1664

(ix) FEATURE:
         (A) NAME/KEY: mat_peptide
         (B) LOCATION: 36..1664

(xi) SEQUENCE DESCRIPTION: SEQ ID NO:3:

TTTTTTTTT TTTTGCGAGT GTTAATTCTA CAATC ATG ATG AAG AGA GAG AAA         53
                                     Met Met Lys Arg Glu Lys
                                      1                   5

AAT GTT ATA TAT GGA CCC GAA CCC CTA CAC C CC TTG GAA GAC AAA ACA    101
Asn Val Ile Tyr Gly Pro Glu Pro Leu His P ro Leu Glu Asp Lys Thr
             10              15                  20

GCA GGA GAA ATG CTC TTC AGG GCC CTT CGA A AA CAT TCT CAT TTA CCG    149
Ala Gly Glu Met Leu Phe Arg Ala Leu Arg L ys His Ser His Leu Pro
             25              30                  35

CAG GCT ATA GTA GAT GTG TTT GGT GAC GAA T CG CTT TCC TAT AAA GAG    197
Gln Ala Ile Val Asp Val Phe Gly Asp Glu S er Leu Ser Tyr Lys Glu
        40              45                  50

TTT TTT GAA GCT ACA TGC CTC CTA GCG CAA A GT CTC CAC AAT TGT GGA    245
Phe Phe Glu Ala Thr Cys Leu Leu Ala Gln S er Leu His Asn Cys Gly
    55              60              65                      70

TAC AAG ATG AAT GAT GTA GTG TCG ATC TGC G CG GAG AAC AAT AAA AGA    293
Tyr Lys Met Asn Asp Val Val Ser Ile Cys A la Glu Asn Asn Lys Arg
             75              80                      85

TTT TTT GTT CCC ATT ATT GCA GCT TGG TAT A TT GGT ATG ATT GTA GCA    341
Phe Phe Val Pro Ile Ile Ala Ala Trp Tyr I le Gly Met Ile Val Ala
             90              95                  100

CCT GTT AAT GAA AGT TAC ATC CCA GAT GAA C TC TGT AAG GTC ATG GGT    389
```

UNITED STATES PATENT AND TRADEMARK OFFICE
CERTIFICATE OF CORRECTION

PATENT NO.       : 6,552,179 B1
APPLICATION NO.  : 08/478205
DATED            : April 22, 2003
INVENTOR(S)      : Keith V. Wood and Monika G. Wood It is certified that error appears in the above-identified patent and that said Letters Patent is hereby corrected as shown below:

```
        Pro Val Asn Glu Ser Tyr Ile Pro Asp Glu L eu Cys Lys Val Met Gly
                    105                 110                115

ATA TCG AAA CCA CAA ATA GTT TTT TGT ACA A AG AAC ATT TTA AAT AAG      437
        Ile Ser Lys Pro Gln Ile Val Phe Cys Thr L ys Asn Ile Leu Asn Lys
                    120                 125                 130

GTA TTG GAG GTA CAG AGC AGA ACT AAT TTC A TA AAA AGG ATC ATC ATA      485
        Val Leu Glu Val Gln Ser Arg Thr Asn Phe I le Lys Arg Ile Ile Ile
        135                 140                 145                 150

CTT GAT ACT GTA GAA AAC ATA CAC GGT TGT G AA AGT CTT CCC AAT TTT      533
        Leu Asp Thr Val Glu Asn Ile His Gly Cys G lu Ser Leu Pro Asn Phe
                    155                 160                 165

ATT TCT CGT TAT TCG GAT GGA AAT ATT GCC A AC TTC AAA CCT TTA CAT      581
        Ile Ser Arg Tyr Ser Asp Gly Asn Ile Ala A sn Phe Lys Pro Leu His
                    170                 175                 180

TAC GAT CCT GTT GAG CAA GTG GCA GCT ATC T TA TGT TCG TCA GGC ACT      629
        Tyr Asp Pro Val Glu Gln Val Ala Ala Ile L eu Cys Ser Ser Gly Thr
                    185                 190                 195

ACT GGA TTA CCG AAA GGT GTA ATG CAA ACT C AC CAA AAT ATT TGT GTC      677
        Thr Gly Leu Pro Lys Gly Val Met Gln Thr H is Gln Asn Ile Cys Val
        200                 205                 210

CGA CTT ATA CAT GCT TTA GAC CCC GAG GCA G GA ACG CAA CTT ATT CCT      725
        Arg Leu Ile His Ala Leu Asp Pro Glu Ala G ly Thr Gln Leu Ile Pro
        215                 220                 225                 230

GGT GTG ACA GTC TTA GTA TAT GTG CCT TTT T TC CAT GCT TTT GGG TTC      773
        Gly Val Thr Val Leu Val Tyr Val Pro Phe P he His Ala Phe Gly Phe
                    235                 240                 245

TCT ATA AAC TTG GGA TAC TTC ATG GTG GGT C TT CGT GTT ATC ATG TTA      821
        Ser Ile Asn Leu Gly Tyr Phe Met Val Gly L eu Arg Val Ile Met Leu
                    250                 255                 260

AGA CGA TTT GAG CAA GAA GCA TTT CTA AAA G CT ATT CAG GAT TAT GAA      869
        Arg Arg Phe Glu Gln Glu Ala Phe Leu Lys A la Ile Gln Asp Tyr Glu
                    265                 270                 275
```

Page 6 of 52

UNITED STATES PATENT AND TRADEMARK OFFICE
CERTIFICATE OF CORRECTION

PATENT NO.       : 6,552,179 B1
APPLICATION NO.  : 08/478205
DATED            : April 22, 2003
INVENTOR(S)      : Keith V. Wood and Monika G. Wood It is certified that error appears in the above-identified patent and that said Letters Patent is hereby corrected as shown below:

```
GTT CGA AGT ATA GTT AAC GTT CCA GCA ATA A TA TTG TTC TTA TCG AAA         917
Val Arg Ser Ile Val Asn Val Pro Ala Ile I le Leu Phe Leu Ser Lys
        280                 285                 290

AGT CCT TTG GTT GAC AAA TAC GAT TTA TCA A GT TTA ACG GAA TTG TGT         965
Ser Pro Leu Val Asp Lys Tyr Asp Leu Ser S er Leu Arg Glu Leu Cys
295                 300                 305                 310

TGC GGT GCG GCA CCA TTA GCA AAG GAA GTT G CT GAG ATT GCA GTA AAA        1013
Cys Gly Ala Ala Pro Leu Ala Lys Glu Val A la Glu Ile Ala Val Lys
                315                 320                 325

CGA TTA AAC TTG CCA GGA ATT CGC TGT GGA T TT GGT TTG ACA GAA TCT        1061
Arg Leu Asn Leu Pro Gly Ile Arg Cys Gly P he Gly Leu Thr Glu Ser
                330                 335                 340

ACT TCA GCT AAT ATA CAC AGT CTT GGG GAT G AA TTT AAA TCA GGA TCA        1109
Thr Ser Ala Asn Ile His Ser Leu Gly Asp G lu Phe Lys Ser Gly Ser
        345                 350                 355

CTT GGA AGA GTT ACT CCT TTA ATG GCA GCT A AA ATA GCA GAT AGG GAA        1157
Leu Gly Arg Val Thr Pro Leu Met Ala Ala L ys Ile Ala Asp Arg Glu
360                 365                 370

ACT GGT AAA GCA TTG GGA CCA AAT CAA GTT G GT GAA TTA TGC ATT AAA        1205
Thr Gly Lys Ala Leu Gly Pro Asn Gln Val G ly Glu Leu Cys Ile Lys
375                 380                 385                 390

GGT CCC ATG GTA TCG AAA GGT TAC GTG AAC A AT GTA GAA GCT ACC AAA        1253
Gly Pro Met Val Ser Lys Gly Tyr Val Asn A sn Val Glu Ala Thr Lys
                395                 400                 405

GAA GCT ATT GAT GAT GAT GGT TGG CTT CAC T CT GGA GAC TTT GGA TAC        1301
Glu Ala Ile Asp Asp Asp Gly Trp Leu His S er Gly Asp Phe Gly Tyr
                410                 415                 420

TAT GAT GAG GAT GAG CAT TTC TAT GTG GTG G AC CGT TAC AAG GAA TTG        1349
Tyr Asp Glu Asp Glu His Phe Tyr Val Val A sp Arg Tyr Lys Glu Leu
        425                 430                 435

ATT AAA TAT AAG GGC TCT CAG GTA GCA CCT G CA GAA CTA GAA GAG ATT        1397
Ile Lys Tyr Lys Gly Ser Gln Val Ala Pro A la Glu Leu Glu Glu Ile
440                 445                 450
```

UNITED STATES PATENT AND TRADEMARK OFFICE
CERTIFICATE OF CORRECTION

PATENT NO.         : 6,552,179 B1
APPLICATION NO.    : 08/478205
DATED              : April 22, 2003
INVENTOR(S)        : Keith V. Wood and Monika G. Wood Page 8 of 52

It is certified that error appears in the above-identified patent and that said Letters Patent is hereby corrected as shown below:

```
TTA TTG AAA AAT CCA TGT ATC AGA GAT GTT G CT GTG GTT GGT ATT CCT        1445
Leu Leu Lys Asn Pro Cys Ile Arg Asp Val A la Val Val Gly Ile Pro
455                 460.                465             470

GAT CTA GAA GCT GGA GAA CTG CCA TCT GCG T TT GTG GTT ATA CAG CCC        1493
Asp Leu Glu Ala Gly Glu Leu Pro Ser Ala P he Val Val Ile Gln Pro
            475                 480              485

GGA AAG GAG ATT ACA GCT AAA GAA GTT TAC G AT TAT CTT GCC GAG AGG        1541
Gly Lys Glu Ile Thr Ala Lys Glu Val Tyr A sp Tyr Leu Ala Glu Arg
            490                 495             500

GTC TCC CAT ACA AAG TAT TTG CGT GGA GGG G TT CGA TTC GTT GAT AGC        1589
Val Ser His Thr Lys Tyr Leu Arg Gly Gly V al Arg Phe Val Asp Ser
        505                 510             515

ATA CCA AGG AAT GTT ACA GGT AAA ATT ACA A GA AAG GAA CTT CTG AAG        1637
Ile Pro Arg Asn Val Thr Gly Lys Ile Thr A rg Lys Glu Leu Leu Lys
    520                 525                 530

CAG TTG CTG GAG AAG AGT TCT AAA CTT TAAAGTCT TC ATGATTATAT             1684
Gln Leu Leu Glu Lys Ser Ser Lys Leu
535                 540

AGAAAAAAAA GCTAGTGATG GGATGTTACC TAGACCAATA TGAAATATTT G GTAAATAAA     1744

TGCTTAATGA ATTTCAAAAA AAAAAA                                           1770

(2) INFORMATION FOR SEQ ID NO:4:

(i) SEQUENCE CHARACTERISTICS:
        (A) LENGTH: 543 amino acids
        (B) TYPE: amino acid
        (D) TOPOLOGY: linear (ii) MOLECULE TYPE: protein
    (xi) SEQUENCE DESCRIPTION: SEQ ID NO:4:

Met Met Lys Arg Glu Lys Asn Val Ile Tyr G ly Pro Glu Pro Leu His
1               5                   10              15
```

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
Pro Leu Glu Asp Lys Thr Ala Gly Glu Met Leu Phe Arg Ala Leu Arg
             20                  25                  30

Lys His Ser His Leu Pro Gln Ala Ile Val Asp Val Phe Gly Asp Glu
             35                  40                  45

Ser Leu Ser Tyr Lys Glu Phe Phe Glu Ala Thr Cys Leu Leu Ala Gln
             50                  55                  60

Ser Leu His Asn Cys Gly Tyr Lys Met Asn Asp Val Val Ser Ile Cys
 65                      70                  75                  80

Ala Glu Asn Asn Lys Arg Phe Phe Val Pro Ile Ile Ala Ala Trp Tyr
                 85                  90                  95

Ile Gly Met Ile Val Ala Pro Val Asn Glu Ser Tyr Ile Pro Asp Glu
                 100                 105                 110

Leu Cys Lys Val Met Gly Ile Ser Lys Pro Gln Ile Val Phe Cys Thr
                 115                 120                 125

Lys Asn Ile Leu Asn Lys Val Leu Glu Val Gln Ser Arg Thr Asn Phe
 130                     135                 140

Ile Lys Arg Ile Ile Ile Leu Asp Thr Val Glu Asn Ile His Gly Cys
145                      150                 155                 160

Glu Ser Leu Pro Asn Phe Ile Ser Arg Tyr Ser Asp Gly Asn Ile Ala
                 165                 170                 175

Asn Phe Lys Pro Leu His Tyr Asp Pro Val Glu Gln Val Ala Ala Ile
                 180                 185                 190

Leu Cys Ser Ser Gly Thr Thr Gly Leu Pro Lys Gly Val Met Gln Thr
                 195                 200                 205

His Gln Asn Ile Cys Val Arg Leu Ile His Ala Leu Asp Pro Glu Ala
 210                     215                 220

Gly Thr Gln Leu Ile Pro Gly Val Thr Val Leu Val Tyr Val Pro Phe
225                      230                 235                 240
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Phe His Ala Phe Gly Phe Ser Ile Asn Leu G ly Tyr Phe Met Val Gly
            245             250                 255

Leu Arg Val Ile Met Leu Arg Arg Phe Glu G ln Glu Ala Phe Leu Lys
            260             265                 270

Ala Ile Gln Asp Tyr Glu Val Arg Ser Ile V al Asn Val Pro Ala Ile
            275             280                 285

Ile Leu Phe Leu Ser Lys Ser Pro Leu Val A sp Lys Tyr Asp Leu Ser
    290             295                 300

Ser Leu Arg Glu Leu Cys Cys Gly Ala Ala P ro Leu Ala Lys Glu Val
305             310                 315                 320

Ala Glu Ile Ala Val Lys Arg Leu Asn Leu P ro Gly Ile Arg Cys Gly
            325             330                 335

Phe Gly Leu Thr Glu Ser Thr Ser Ala Asn I le His Ser Leu Gly Asp
            340             345                 350

Glu Phe Lys Ser Gly Ser Leu Gly Arg Val T hr Pro Leu Met Ala Ala
        355             360                 365

Lys Ile Ala Asp Arg Glu Thr Gly Lys Ala L eu Gly Pro Asn Gln Val
            370             375             380

Gly Glu Leu Cys Ile Lys Gly Pro Met Val S er Lys Gly Tyr Val Asn
385             390             395                 400

Asn Val Glu Ala Thr Lys Glu Ala Ile Asp A sp Asp Gly Trp Leu His
                405             410                 415

Ser Gly Asp Phe Gly Tyr Tyr Asp Glu Asp G lu His Phe Tyr Val Val
            420             425                 430

Asp Arg Tyr Lys Glu Leu Ile Lys Tyr Lys G ly Ser Gln Val Ala Pro
            435             440                 445

Ala Glu Leu Glu Glu Ile Leu Leu Lys Asn P ro Cys Ile Arg Asp Val
    450             455                 460
```

UNITED STATES PATENT AND TRADEMARK OFFICE
CERTIFICATE OF CORRECTION

PATENT NO.     : 6,552,179 B1
APPLICATION NO. : 08/478205
DATED          : April 22, 2003
INVENTOR(S)    : Keith V. Wood and Monika G. Wood It is certified that error appears in the above-identified patent and that said Letters Patent is hereby corrected as shown below:

```
     Ala Val Val Gly Ile Pro Asp Leu Glu Ala G ly Glu Leu Pro Ser Ala
     465             470             475             480

Phe Val Val Ile Gln Pro Gly Lys Glu Ile T hr Ala Lys Glu Val Tyr
                     485             490             495

Asp Tyr Leu Ala Glu Arg Val Ser His Thr L ys Tyr Leu Arg Gly Gly
                     500             505             510

Val Arg Phe Val Asp Ser Ile Pro Arg Asn V al Thr Gly Lys Ile Thr
                     515             520             525

Arg Lys Glu Leu Leu Lys Gln Leu Leu Glu L ys Ser Ser Lys Leu
                     530             535             540

(2) INFORMATION FOR SEQ ID NO:5:

(i) SEQUENCE CHARACTERISTICS:
        (A) LENGTH: 1764 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 30..1658

(ix) FEATURE:
        (A) NAME/KEY: mat_ peptide
        (B) LOCATION: 30..1658

(xi) SEQUENCE DESCRIPTION: SEQ ID NO:5:

TTTTTTTTGC GAGTGTTAAT TCTACAATC ATG ATG AAG AGA GA G AAA AAT GTT       53
                                Met Met L ys Arg Glu Lys Asn Val
                                 1                   5

ATA TAT GGA CCC GAA CCC CTA CAC CCC TTG G AA GAC AAA ACA GCA GGA     101
Ile Tyr Gly Pro Glu Pro Leu His Pro Leu G lu Asp Lys Thr Ala Gly
 10              15                  20

GAA ATG CTC TTC AGG GCC CTT CGA AAA CAT T CT CAT TTA CCG CAG GCT     149
Glu Met Leu Phe Arg Ala Leu Arg Lys His S er His Leu Pro Gln Ala
 25              30              35                  40
```

UNITED STATES PATENT AND TRADEMARK OFFICE
CERTIFICATE OF CORRECTION

PATENT NO.      : 6,552,179 B1                                              Page 12 of 52
APPLICATION NO. : 08/478205
DATED           : April 22, 2003
INVENTOR(S)     : Keith V. Wood and Monika G. Wood It is certified that error appears in the above-identified patent and that said Letters Patent is hereby corrected as shown below:

```
ATA GTA GAT GTG TTT GGT GAC GAA TCG CTT T CC TAT AAA GAG TTT TTT     197
Ile Val Asp Val Phe Gly Asp Glu Ser Leu S er Tyr Lys Glu Phe Phe
            45                      50                  55

GAA GCT ACA TGC CTC CTA GCG CAA AGT CTC C AC AAT TGT GGA TAC AAG     245
Glu Ala Thr Cys Leu Leu Ala Gln Ser Leu H is Asn Cys Gly Tyr Lys
        60                      65                  70

ATG AAT GAT GTA GTG TCG ATC TGC GCG GAG A AC AAT AAA AGA TTT TTT     293
Met Asn Asp Val Val Ser Ile Cys Ala Glu A sn Asn Lys Arg Phe Phe
        75                      80                  85

GTT CCC ATT ATT GCA GCT TGG TAT ATT GGT A TG ATT GTA GCA CCT GTT     341
Val Pro Ile Ile Ala Ala Trp Tyr Ile Gly M et Ile Val Ala Pro Val
        90                      95                  100

AAT GAA AGT TAC ATC CCA GAT GAA CTC TGT A AG GTC ATG GGT ATA TCG     389
Asn Glu Ser Tyr Ile Pro Asp Glu Leu Cys L ys Val Met Gly Ile Ser
105                 110                 115                 120

AAA CCA CAA ATA GTT TTT TGT ACA AAG AAC A TT TTA AAT AAG GTA TTG     437
Lys Pro Gln Ile Val Phe Cys Thr Lys Asn I le Leu Asn Lys Val Leu
                125                 130                 135

GAG GTA CAG AGC AGA ACT AAT TTC ATA AAA A GG ATC ATA CTT GAT         485
Glu Val Gln Ser Arg Thr Asn Phe Ile Lys A rg Ile Ile Leu Asp
            140                 145                 150

ACT GTA GAA AAC ATA CAC GGT TGT GAA AGT C TT CCC AAT TTT ATT TCT     533
Thr Val Glu Asn Ile His Gly Cys Glu Ser L eu Pro Asn Phe Ile Ser
        155                 160                 165

CGT TAT TCG GAT GGA AAT ATT GCC AAC TTC A AA CCT TTA CAT TAC GAT     581
Arg Tyr Ser Asp Gly Asn Ile Ala Asn Phe L ys Pro Leu His Tyr Asp
        170                 175                 180

CCT GTT GAG CAA GTG GCA GCT ATC TTA TGT T CG TCA GGC ACT ACT GGA     629
Pro Val Glu Gln Val Ala Ala Ile Leu Cys S er Ser Gly Thr Thr Gly
185                 190                 195                 200

TTA CCG AAA GGT GTA ATG CAA ACT CAC CAA A AT ATT TGT GTC CGA CTT     677
Leu Pro Lys Gly Val Met Gln Thr His Gln A sn Ile Cys Val Arg Leu
            205                 210                 215
```

UNITED STATES PATENT AND TRADEMARK OFFICE
CERTIFICATE OF CORRECTION

| | |
|---|---|
| PATENT NO. | : 6,552,179 B1 |
| APPLICATION NO. | : 08/478205 |
| DATED | : April 22, 2003 |
| INVENTOR(S) | : Keith V. Wood and Monika G. Wood |

Page 13 of 52

It is certified that error appears in the above-identified patent and that said Letters Patent is hereby corrected as shown below:

```
ATA CAT GCT TTA GAC CCC GAG GCA GGA ACG C AA CTT ATT CCT GGT GTG      725
Ile His Ala Leu Asp Pro Glu Ala Gly Thr G ln Leu Ile Pro Gly Val
            220                 225                 230

ACA GTC TTA GTA TAT GTG CCT TTT TTC CAT G CT TTT GGG TTC TCT ATA      773
Thr Val Leu Val Tyr Val Pro Phe Phe His A la Phe Gly Phe Ser Ile
            235                 240                 245

AAC TTG GGA TAC TTC ATG GTG GGT CTT CGT G TT ATC ATG TTA AGA CGA      821
Asn Leu Gly Tyr Phe Met Val Gly Leu Arg V al Ile Met Leu Arg Arg
            250                 255                 260

TTT GAG CAA GAA GCA TTT CTA AAA GCT ATT C AG GAT TAT GAA GTT CGA      869
Phe Glu Gln Glu Ala Phe Leu Lys Ala Ile G ln Asp Tyr Glu Val Arg
265                 270                 275                 280

AGT ATA GTT AAC GTT CCA GCA ATA ATA TTG T TC TTA TCG AAA AGT CCT      917
Ser Ile Val Asn Val Pro Ala Ile Ile Leu P he Leu Ser Lys Ser Pro
                285                 290                 295

TTG GTT GAC AAA TAC GAT TTA TCA AGT TTA A GG GAA TTG TGT TGC GGT      965
Leu Val Asp Lys Tyr Asp Leu Ser Ser Leu A rg Glu Leu Cys Cys Gly
                300                 305                 310

GCG GCA CCA TTA GCA AAG GAA GTT GCT GAG A TT GCA GTA AAA CGA TTA     1013
Ala Ala Pro Leu Ala Lys Glu Val Ala Glu I le Ala Val Lys Arg Leu
            315                 320                 325

AAC TTG CCA GGA ATT CGC TGT GGA TTT GGT T TG ACA GAA TCT ACT TCA     1061
Asn Leu Pro Gly Ile Arg Cys Gly Phe Gly L eu Thr Glu Ser Thr Ser
            330                 335                 340

GCT AAT ATA CAC AGT CTT GGG GAT GAA TTT A AA TCA GGA TCA CTT GGA     1109
Ala Asn Ile His Ser Leu Gly Asp Glu Phe L ys Ser Gly Ser Leu Gly
345                 350                 355                 360

AGA GTT ACT CCT TTA ATG GCA GCT AAA ATA G CA GAT AGG GAA ACT GGT     1157
Arg Val Thr Pro Leu Met Ala Ala Lys Ile A la Asp Arg Glu Thr Gly
                365                 370                 375
```

UNITED STATES PATENT AND TRADEMARK OFFICE
CERTIFICATE OF CORRECTION

PATENT NO.       : 6,552,179 B1
APPLICATION NO.  : 08/478205
DATED            : April 22, 2003
INVENTOR(S)      : Keith V. Wood and Monika G. Wood It is certified that error appears in the above-identified patent and that said Letters Patent is hereby corrected as shown below:

```
AAA GCA TTG GGA CCA AAT CAA GTT GGT GAA T TA TGC ATT AAA GGT CCC       1205
Lys Ala Leu Gly Pro Asn Gln Val Gly Glu L eu Cys Ile Lys Gly Pro
            380                 385             390

ATG GTA TCG AAA GGT TAC GTG AAC AAT GTA G AA GCT ACC AAA GAA GCT       1253
Met Val Ser Lys Gly Tyr Val Asn Asn Val G lu Ala Thr Lys Glu Ala
        395                 400             405

ATT GAT GAT GAT GGT TGG CTT CAC TCT GGA G AC TTT GGA TAC TAT GAT       1301
Ile Asp Asp Asp Gly Trp Leu His Ser Gly A sp Phe Gly Tyr Tyr Asp
        410                 415                 420

GAG GAT GAG CAT TTC TAT GTG GTG GAC CGT T AC AAG GAA TTG ATT AAA       1349
Glu Asp Glu His Phe Tyr Val Val Asp Arg T yr Lys Glu Leu Ile Lys
425                 430                 435                 440

TAT AAG GGC TCT CAG GTA GCA CCT GCA GAA C TA GAA GAG ATT TTA TTG       1397
Tyr Lys Gly Ser Gln Val Ala Pro Ala Glu L eu Glu Glu Ile Leu Leu
            445                 450                 455

AAA AAT CCA TGT ATC AGA GAT GTT GCT GTG G TT GGT ATT CCT GAT CTA       1445
Lys Asn Pro Cys Ile Arg Asp Val Ala Val V al Gly Ile Pro Asp Leu
            460                 465                 470

GAA GCT GGA GAA CTG CCA TCT GCG TTT GTG G TT ATA CAG CCC GGA AAG       1493
Glu Ala Gly Glu Leu Pro Ser Ala Phe Val V al Ile Gln Pro Gly Lys
            475                 480                 485

GAG ATT ACA GCT AAA GAA GTT TAC GAT TAT C TT GCC GAG AGG GTC TCC       1541
Glu Ile Thr Ala Lys Glu Val Tyr Asp Tyr L eu Ala Glu Arg Val Ser
        490                 495                 500

CAT ACA AAG TAT TTG CGT GGA GGG GTT CGA T TC GTT GAT AGC ATA CCA       1589
His Thr Lys Tyr Leu Arg Gly Gly Val Arg P he Val Asp Ser Ile Pro
505                 510                 515                 520

AGG AAT GTT ACA GGT AAA ATT ACA AGA AAG G AA CTT CTG AAG CAG TTG       1637
Arg Asn Val Thr Gly Lys Ile Thr Arg Lys G lu Leu Leu Lys Gln Leu
            525                 530                 535

CTG GAG AAG AGT TCT AAA CTT TAAAGTCTTC ATGATTAT AT AGAAAAAAAA          1688
Leu Glu Lys Ser Ser Lys Leu
                540
```

UNITED STATES PATENT AND TRADEMARK OFFICE
CERTIFICATE OF CORRECTION

PATENT NO.         : 6,552,179 B1
APPLICATION NO. : 08/478205
DATED                  : April 22, 2003
INVENTOR(S)       : Keith V. Wood and Monika G. Wood It is certified that error appears in the above-identified patent and that said Letters Patent is hereby corrected as shown below:

```
GCTAGTGATG GGATGTTACC TAGACCAATA TGAAATATTT GGTAAATAAA T GCTTAATGA    1748

ATTTCAAAAA AAAAAA                                                     1764

(2) INFORMATION FOR SEQ ID NO:6:

(i) SEQUENCE CHARACTERISTICS:
        (A) LENGTH: 543 amino acids
        (B) TYPE: amino acid
        (D) TOPOLOGY: linear (ii) MOLECULE TYPE: protein (xi) SEQUENCE DESCRIPTION: SEQ ID NO:6:

Met Met Lys Arg Glu Lys Asn Val Ile Tyr G ly Pro Glu Pro Leu His
 1               5                  10                  15

Pro Leu Glu Asp Lys Thr Ala Gly Glu Met L eu Phe Arg Ala Leu Arg
            20                  25                  30

Lys His Ser His Leu Pro Gln Ala Ile Val A sp Val Phe Gly Asp Glu
        35                  40                  45

Ser Leu Ser Tyr Lys Glu Phe Phe Glu Ala T hr Cys Leu Leu Ala Gln
    50                  55                  60

Ser Leu His Asn Cys Gly Tyr Lys Met Asn A sp Val Val Ser Ile Cys
65                  70                  75                  80

Ala Glu Asn Asn Lys Arg Phe Phe Val Pro I le Ile Ala Ala Trp Tyr
                85                  90                  95

Ile Gly Met Ile Val Ala Pro Val Asn Glu S er Tyr Ile Pro Asp Glu
            100                 105                 110

Leu Cys Lys Val Met Gly Ile Ser Lys Pro G ln Ile Val Phe Cys Thr
        115                 120                 125
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Lys Asn Ile Leu Asn Lys Val Leu Glu Val G ln Ser Arg Thr Asn Phe
    130             135             140
Ile Lys Arg Ile Ile Ile Leu Asp Thr Val G lu Asn Ile His Gly Cys
145             150             155             160
Glu Ser Leu Pro Asn Phe Ile Ser Arg Tyr S er Asp Gly Asn Ile Ala
                165             170             175
Asn Phe Lys Pro Leu His Tyr Asp Pro Val G lu Gln Val Ala Ala Ile
            180             185             190
Leu Cys Ser Ser Gly Thr Thr Gly Leu Pro L ys Gly Val Met Gln Thr
        195             200             205
His Gln Asn Ile Cys Val Arg Leu Ile His A la Leu Asp Pro Glu Ala
    210             215             220
Gly Thr Gln Leu Ile Pro Gly Val Thr Val L eu Val Tyr Val Pro Phe
225             230             235             240
Phe His Ala Phe Gly Phe Ser Ile Asn Leu G ly Tyr Phe Met Val Gly
                245             250             255
Leu Arg Val Ile Met Leu Arg Arg Phe Glu G ln Glu Ala Phe Leu Lys
            260             265             270
Ala Ile Gln Asp Tyr Glu Val Arg Ser Ile V al Asn Val Pro Ala Ile
        275             280             285
Ile Leu Phe Leu Ser Lys Ser Pro Leu Val A sp Lys Tyr Asp Leu Ser
    290             295             300
Ser Leu Arg Glu Leu Cys Cys Gly Ala Ala P ro Leu Ala Lys Glu Val
305             310             315             320
Ala Glu Ile Ala Val Lys Arg Leu Asn Leu P ro Gly Ile Arg Cys Gly
                325             330             335
Phe Gly Leu Thr Glu Ser Thr Ser Ala Asn I le His Ser Leu Gly Asp
            340             345             350
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood Page 17 of 52

It is certified that error appears in the above-identified patent and that said Letters Patent is hereby corrected as shown below:

```
Glu Phe Lys Ser Gly Ser Leu Gly Arg Val Thr Pro Leu Met Ala Ala
        355             360             365
Lys Ile Ala Asp Arg Glu Thr Gly Lys Ala Leu Gly Pro Asn Gln Val
        370             375             380
Gly Glu Leu Cys Ile Lys Gly Pro Met Val Ser Lys Gly Tyr Val Asn
385             390             395             400
Asn Val Glu Ala Thr Lys Glu Ala Ile Asp Asp Asp Gly Trp Leu His
                405             410             415
Ser Gly Asp Phe Gly Tyr Tyr Asp Glu Asp Glu His Phe Tyr Val Val
            420             425             430
Asp Arg Tyr Lys Glu Leu Ile Lys Tyr Lys Gly Ser Gln Val Ala Pro
        435             440             445
Ala Glu Leu Glu Glu Ile Leu Leu Lys Asn Pro Cys Ile Arg Asp Val
        450             455             460
Ala Val Val Gly Ile Pro Asp Leu Glu Ala Gly Glu Leu Pro Ser Ala
465             470             475             480
Phe Val Val Ile Gln Pro Gly Lys Glu Ile Thr Ala Lys Glu Val Tyr
            485             490             495
Asp Tyr Leu Ala Glu Arg Val Ser His Thr Lys Tyr Leu Arg Gly Gly
            500             505             510
Val Arg Phe Val Asp Ser Ile Pro Arg Asn Val Thr Gly Lys Ile Thr
        515             520             525
Arg Lys Glu Leu Leu Lys Gln Leu Leu Glu Lys Ser Ser Lys Leu
        530             535             540

(2) INFORMATION FOR SEQ ID NO:7:

(i) SEQUENCE CHARACTERISTICS:
        (A) LENGTH: 1766 base pairs
        (B) TYPE: nucleic acid
        (C) STRANDEDNESS: single
        (D) TOPOLOGY: linear
```

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
    (ix) FEATURE:
         (A) NAME/KEY: CDS
         (B) LOCATION: 32..1660

(ix) FEATURE:
         (A) NAME/KEY: mat_peptide
         (B) LOCATION: 32..1660

(xi) SEQUENCE DESCRIPTION: SEQ ID NO:7:

TTTTTTTTTT GCGAGTGTTA ATTCTACAAT C ATG ATG AAG AGA  GAG AAA AAT          52
                                   Met Met Lys Arg  Glu Lys Asn
                                    1                5

GTT ATA TAT GGA CCC GAA CCC CTA CAC CCC T TG GAA GAC AAA ACA GCA        100
 Val Ile Tyr Gly Pro Glu Pro Leu His Pro L eu Glu Asp Lys Thr Ala
          10              15                  20

GGA GAA ATG CTC TTC AGG GCC CTT CGA AAA C AT TCT CAT TTA CCG CAG        148
 Gly Glu Met Leu Phe Arg Ala Leu Arg Lys H is Ser His Leu Pro Gln
          25              30                  35

GCT ATA GTA GAT GTG TTT GGT GAC GAA TCG C TT TCC TAT AAA GAG TTT        196
 Ala Ile Val Asp Val Phe Gly Asp Glu Ser L eu Ser Tyr Lys Glu Phe
  40              45              50               55

TTT GAA GCT ACA TGC CTC CTA GCG CAA AGT C TC CAC AAT TGT GGA TAC        244
 Phe Glu Ala Thr Cys Leu Leu Ala Gln Ser L eu His Asn Cys Gly Tyr
                  60              65                  70

AAG ATG AAT GAT GTA GTG TCG ATC TGC GCG G AG AAC AAT AAA AGA TTT        292
 Lys Met Asn Asp Val Val Ser Ile Cys Ala G lu Asn Asn Lys Arg Phe
                      75              80              85

TTT ATT CCC ATT ATT GCA GCT TGG TAT ATT G GT ATG ATT GTA GCA CCT        340
 Phe Ile Pro Ile Ile Ala Ala Trp Tyr Ile G ly Met Ile Val Ala Pro
                  90              95                 100
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
GTT AAT GAA AGT TAC ATC CCA GAT GAA CTC T GT AAG GTC ATG GGT ATA      388
Val Asn Glu Ser Tyr Ile Pro Asp Glu Leu C ys Lys Val Met Gly Ile
    105             110                 115

TCG AAA CCA CAA ATA GTT TTT TGT ACA AAG A AC ATT TTA AAT AAG GTA      436
Ser Lys Pro Gln Ile Val Phe Cys Thr Lys A sn Ile Leu Asn Lys Val
120             125                 130                 135

TTG GAG GTA CAG AGC AGA ACT AAT TTC ATA A AA AGG ATC ATC ATA CTT      484
Leu Glu Val Gln Ser Arg Thr Asn Phe Ile L ys Arg Ile Ile Ile Leu
            140                 145                 150

GAT ACT GTA GAA AAC ATA CAC GGT TGT GAA A GT CTT CCC AAT TTT ATT      532
Asp Thr Val Glu Asn Ile His Gly Cys Glu S er Leu Pro Asn Phe Ile
        155                 160                 165

TCT CGT TAT TCG GAT GGA AAT ATT GCC AAC T TC AAA CCT TTA CAT TAC      580
Ser Arg Tyr Ser Asp Gly Asn Ile Ala Asn P he Lys Pro Leu His Tyr
        170                 175                 180

GAT CCT GTT GAG CAA GTG GCA GCT ATC TTA T GT TCG TCA GGC ACT ACT      628
Asp Pro Val Glu Gln Val Ala Ala Ile Leu C ys Ser Ser Gly Thr Thr
        185                 190                 195

GGA TTA CCG AAA GGT GTA ATG CAA ACT CAC C AA AAT ATT TGT GTC CGA      676
Gly Leu Pro Lys Gly Val Met Gln Thr His G ln Asn Ile Cys Val Arg
200                 205                 210                 215

CTT ATA CAT GCT TTA GAC CCC GAG GCA GGA A CG CAA CTT ATT CCT GGT      724
Leu Ile His Ala Leu Asp Pro Glu Ala Gly T hr Gln Leu Ile Pro Gly
                220                 225                 230

GTG ACA GTC TTA GTA TAT GTG CCT TTT TTC C AT GCT TTT GGG TTC GGT      772
Val Thr Val Leu Val Tyr Val Pro Phe Phe H is Ala Phe Gly Phe Gly
            235                 240                 245

ATA AAC TTG GGA TAC TTC ATG GTG GGT CTT C GT GTT ATC ATG TTA AGA      820
Ile Asn Leu Gly Tyr Phe Met Val Gly Leu A rg Val Ile Met Leu Arg
            250                 255                 260
```

UNITED STATES PATENT AND TRADEMARK OFFICE
CERTIFICATE OF CORRECTION

PATENT NO.         : 6,552,179 B1
APPLICATION NO.    : 08/478205
DATED              : April 22, 2003
INVENTOR(S)        : Keith V. Wood and Monika G. Wood It is certified that error appears in the above-identified patent and that said Letters Patent is hereby corrected as shown below:

```
CGA TTT GAG CAA GAA GCA TTT CTA AAA GCT A TT CAG GAT TAT GAA GTT       868
Arg Phe Glu Gln Glu Ala Phe Leu Lys Ala I le Gln Asp Tyr Glu Val
265                     270                 275

CGA AGT ATA GTT AAC GTT CCA GCA ATA ATA T TG TTC TTA TCG AAA AGT       916
Arg Ser Ile Val Asn Val Pro Ala Ile Ile L eu Phe Leu Ser Lys Ser
280                     285                 290                 295

CCT TTG GTT GAC AAA TAC GAT TTA TCA AGT T TA AGG GAA TTG TGT TGC       964
Pro Leu Val Asp Lys Tyr Asp Leu Ser Ser L eu Arg Glu Leu Cys Cys
                300                 305                 310

GGT GCG GCA CCA TTA GCA AAG GAA GTT GCT G AG ATT GCA GTA AAA CGA      1012
Gly Ala Ala Pro Leu Ala Lys Glu Val Ala G lu Ile Ala Val Lys Arg
            315                 320                 325

TTA AAC TTG CCA GGA ATT CGC TGT GGA TTT G GT TTG ACA GAA TCT ACT      1060
Leu Asn Leu Pro Gly Ile Arg Cys Gly Phe G ly Leu Thr Glu Ser Thr
        330                 335                 340

TCA GCT AAT ATA CAC AGT CTT GGG GAT GAA T TT AAA TCA GGA TCA CTT      1108
Ser Ala Asn Ile His Ser Leu Gly Asp Glu P he Lys Ser Gly Ser Leu
    345                 350                 355

GGA AGA GTT ACT CCT TTA ATG GCA GCT AAA A TA GCA GAT AGG GAA ACT      1156
Gly Arg Val Thr Pro Leu Met Ala Ala Lys I le Ala Asp Arg Glu Thr
360                 365                 370                 375

GGT AAA GCA TTG GGA CCA AAT CAA GTT GGT G AA TTA TGC ATT AAA GGT      1204
Gly Lys Ala Leu Gly Pro Asn Gln Val Gly G lu Leu Cys Ile Lys Gly
                380                 385                 390

CCC ATG GTA TCG AAA GGT TAC GTG AAC AAT G TA AAA GCT ACC AAA GAA      1252
Pro Met Val Ser Lys Gly Tyr Val Asn Asn V al Lys Ala Thr Lys Glu
            395                 400                 405

GCT ATT GAT GAT GAT GGT TGG CTT CAC TCT G GA GAC TTT GGA TAC TAT      1300
Ala Ile Asp Asp Asp Gly Trp Leu His Ser G ly Asp Phe Gly Tyr Tyr
        410                 415                 420
```

Page 20 of 52

UNITED STATES PATENT AND TRADEMARK OFFICE
CERTIFICATE OF CORRECTION

PATENT NO. : 6,552,179 B1  
APPLICATION NO. : 08/478205  
DATED : April 22, 2003  
INVENTOR(S) : Keith V. Wood and Monika G. Wood It is certified that error appears in the above-identified patent and that said Letters Patent is hereby corrected as shown below:

```
GAT GAG GAT GAG CAT TTC TAT GTG GTG GAC C GT TAC AAG GAA TTG ATT      1348
Asp Glu Asp Glu His Phe Tyr Val Val Asp A rg Tyr Lys Glu Leu Ile
    425                 430                 435

AAA TAT AAG GGC TCT CAG GTA GCA CCT GCA G AA CTA GAA GAG ATT TTA      1396
Lys Tyr Lys Gly Ser Gln Val Ala Pro Ala G lu Leu Glu Glu Ile Leu
440                 445                 450                 455

TTG AAA AAT CCA TGT ATC AGA GAT GTT GCT G TG GTT GGT ATT CCT GAT      1444
Leu Lys Asn Pro Cys Ile Arg Asp Val Ala V al Val Gly Ile Pro Asp
                460                 465                 470

CTA GAA GCT GGA GAA CTG CCA TCT GCG TTT G TG GTT ATA CAG CCC GGA      1492
Leu Glu Ala Gly Glu Leu Pro Ser Ala Phe V al Val Ile Gln Pro Gly
            475                 480                 485

AAG GAG ATT ACA GCT AAA GAA GTT TAC GAT T AT CTT GCC GAG AGG GTC      1540
Lys Glu Ile Thr Ala Lys Glu Val Tyr Asp T yr Leu Ala Glu Arg Val
        490                 495                 500

TCC CAT ACA AAG TAT TTG CGT GGA GGG GTT C GA TTC GTT GAT AGC ATA      1588
Ser His Thr Lys Tyr Leu Arg Gly Gly Val A rg Phe Val Asp Ser Ile
    505                 510                 515

CCA AGG AAT GTT ACA GGT AAA ATT ACA AGA A AG GAA CTT CTG AAG CAG      1636
Pro Arg Asn Val Thr Gly Lys Ile Thr Arg L ys Glu Leu Leu Lys Gln
520                 525                 530                 535

TTG CTG GAG AAG AGT TCT AAA CTT TAAAGTCTTC A TGATTATAT AGAAAAAAAA     1690
Leu Leu Glu Lys Ser Ser Lys Leu
                540

GCTAGTGATG GGATGTTACC TAGACCAATA TGAAATATTT GGTAAATAAA T GCTTAATGA   1750

ATTTCAAAAA AAAAAA                                                     1766
```

UNITED STATES PATENT AND TRADEMARK OFFICE
CERTIFICATE OF CORRECTION

PATENT NO.         : 6,552,179 B1
APPLICATION NO. : 08/478205
DATED                 : April 22, 2003
INVENTOR(S)       : Keith V. Wood and Monika G. Wood It is certified that error appears in the above-identified patent and that said Letters Patent is hereby corrected as shown below:

```
(2) INFORMATION FOR SEQ ID NO:8:

(i) SEQUENCE CHARACTERISTICS:
        (A) LENGTH: 543 amino acids
        (B) TYPE: amino acid
        (D) TOPOLOGY: linear (ii) MOLECULE TYPE: protein (xi) SEQUENCE DESCRIPTION: SEQ ID NO:8:

Met Met Lys Arg Glu Lys Asn Val Ile Tyr G ly Pro Glu Pro Leu His
 1               5                  10                 15

Pro Leu Glu Asp Lys Thr Ala Gly Glu Met L eu Phe Arg Ala Leu Arg
            20                  25                 30

Lys His Ser His Leu Pro Gln Ala Ile Val A sp Val Phe Gly Asp Glu
        35                  40                 45

Ser Leu Ser Tyr Lys Glu Phe Phe Glu Ala T hr Cys Leu Leu Ala Gln
    50                  55                 60

Ser Leu His Asn Cys Gly Tyr Lys Met Asn A sp Val Val Ser Ile Cys
65                  70                  75                 80

Ala Glu Asn Asn Lys Arg Phe Phe Ile Pro I le Ile Ala Ala Trp Tyr
                85                  90                 95

Ile Gly Met Ile Val Ala Pro Val Asn Glu S er Tyr Ile Pro Asp Glu
            100                 105                110

Leu Cys Lys Val Met Gly Ile Ser Lys Pro G ln Ile Val Phe Cys Thr
            115                 120                125

Lys Asn Ile Leu Asn Lys Val Leu Glu Val G ln Ser Arg Thr Asn Phe
        130                 135                140

Ile Lys Arg Ile Ile Ile Leu Asp Thr Val G lu Asn Ile His Gly Cys
145                 150                 155                160
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Glu Ser Leu Pro Asn Phe Ile Ser Arg Tyr S er Asp Gly Asn Ile Ala
            165             170             175

Asn Phe Lys Pro Leu His Tyr Asp Pro Val G lu Gln Val Ala Ala Ile
            180             185             190

Leu Cys Ser Ser Gly Thr Thr Gly Leu Pro L ys Gly Val Met Gln Thr
            195             200             205

His Gln Asn Ile Cys Val Arg Leu Ile His A la Leu Asp Pro Glu Ala
        210             215             220

Gly Thr Gln Leu Ile Pro Gly Val Thr Val L eu Val Tyr Val Pro Phe
225             230             235             240

Phe His Ala Phe Gly Phe Gly Ile Asn Leu G ly Tyr Phe Met Val Gly
            245             250             255

Leu Arg Val Ile Met Leu Arg Arg Phe Glu G ln Glu Ala Phe Leu Lys
            260             265             270

Ala Ile Gln Asp Tyr Glu Val Arg Ser Ile V al Asn Val Pro Ala Ile
        275             280             285

Ile Leu Phe Leu Ser Lys Ser Pro Leu Val A sp Lys Tyr Asp Leu Ser
        290             295             300

Ser Leu Arg Glu Leu Cys Cys Gly Ala Ala P ro Leu Ala Lys Glu Val
305             310             315             320

Ala Glu Ile Ala Val Lys Arg Leu Asn Leu P ro Gly Ile Arg Cys Gly
            325             330             335

Phe Gly Leu Thr Glu Ser Thr Ser Ala Asn I le His Ser Leu Gly Asp
            340             345             350

Glu Phe Lys Ser Gly Ser Leu Gly Arg Val T hr Pro Leu Met Ala Ala
            355             360             365

Lys Ile Ala Asp Arg Glu Thr Gly Lys Ala L eu Gly Pro Asn Gln Val
        370             375             380

Gly Glu Leu Cys Ile Lys Gly Pro Met Val S er Lys Gly Tyr Val Asn
385             390             395             400
```

UNITED STATES PATENT AND TRADEMARK OFFICE
CERTIFICATE OF CORRECTION

PATENT NO.        : 6,552,179 B1
APPLICATION NO. : 08/478205
DATED             : April 22, 2003
INVENTOR(S)      : Keith V. Wood and Monika G. Wood It is certified that error appears in the above-identified patent and that said Letters Patent is hereby corrected as shown below:

```
Asn Val Lys Ala Thr Lys Glu Ala Ile Asp Asp Asp Gly Trp Leu His
                405             410              415

Ser Gly Asp Phe Gly Tyr Tyr Asp Glu Asp Glu His Phe Tyr Val Val
            420             425             430

Asp Arg Tyr Lys Glu Leu Ile Lys Tyr Lys Gly Ser Gln Val Ala Pro
            435             440              445

Ala Glu Leu Glu Glu Ile Leu Leu Lys Asn Pro Cys Ile Arg Asp Val
450             455             460

Ala Val Val Gly Ile Pro Asp Leu Glu Ala Gly Glu Leu Pro Ser Ala
465             470             475             480

Phe Val Val Ile Gln Pro Gly Lys Glu Ile Thr Ala Lys Glu Val Tyr
                485             490             495

Asp Tyr Leu Ala Glu Arg Val Ser His Thr Lys Tyr Leu Arg Gly Gly
            500             505             510

Val Arg Phe Val Asp Ser Ile Pro Arg Asn Val Thr Gly Lys Ile Thr
            515             520             525

Arg Lys Glu Leu Leu Lys Gln Leu Leu Glu Lys Ser Ser Lys Leu
        530             535             540

(2) INFORMATION FOR SEQ ID NO:9:

(i) SEQUENCE CHARACTERISTICS:
        (A) LENGTH: 1838 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 52..1701
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
(ix) FEATURE:
    (A) NAME/KEY: mat_peptide
    (B) LOCATION: 52..1701

(xi) SEQUENCE DESCRIPTION: SEQ ID NO:9:

ATTCTTGAAT GTCGCTCGCA GTGACATTAG CATTCCGGTA CTGTTGGTAA A  ATG GAA        57
                                                         Met Glu
                                                          1

GAC GCC AAA AAC ATA AAG AAA GGC CCG GCG C CA TTC TAT CCT CTA GAG       105
Asp Ala Lys Asn Ile Lys Lys Gly Pro Ala P ro Phe Tyr Pro Leu Glu
             5                  10                  15

GAT GGA ACC GCT GGA GAG CAA CTG CAT AAG G CT ATG AAG AGA TAC GCC       153
Asp Gly Thr Ala Gly Glu Gln Leu His Lys A la Met Lys Arg Tyr Ala
         20                  25                  30

CTG GTT CCT GGA ACA ATT GCT TTT ACA GAT G CA CAT ATC GAG GTG AAC       201
Leu Val Pro Gly Thr Ile Ala Phe Thr Asp A la His Ile Glu Val Asn
     35                  40                  45                  50

ATC ACG TAC GCG GAA TAC TTC GAA ATG TCC G TT CGG TTG GCA GAA GCT       249
Ile Thr Tyr Ala Glu Tyr Phe Glu Met Ser V al Arg Leu Ala Glu Ala
                 55                  60                  65

ATG AAA CGA TAT GGG CTG AAT ACA AAT CAC A GA ATC GTC GTA TGC AGT       297
Met Lys Arg Tyr Gly Leu Asn Thr Asn His A rg Ile Val Val Cys Ser
             70                  75                  80

GAA AAC TCT CTT CAA TTC TTT ATG CCG GTG T TG GGC GCG TTA TTT ATC       345
Glu Asn Ser Leu Gln Phe Phe Met Pro Val L eu Gly Ala Leu Phe Ile
         85                  90                  95

GGA GTT GCA GTT GCG CCC GCG AAC GAC ATT T AT AAT GAA CGT GAA TTG       393
Gly Val Ala Val Ala Pro Ala Asn Asp Ile T yr Asn Glu Arg Glu Leu
     100                 105                 110
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
CTC AAC AGT ATG AAC ATT TCG CAG CCT ACC G TA GTG TTT GTT TCC AAA      441
Leu Asn Ser Met Asn Ile Ser Gln Pro Thr V al Val Phe Val Ser Lys
115                 120                 125                 130

AAG GGG TTG CAA AAA ATT TTG AAC GTG CAA A AA AAA TTA CCA ATA ATC      489
Lys Gly Leu Gln Lys Ile Leu Asn Val Gln L ys Lys Leu Pro Ile Ile
                    135                 140                 145

CAG AAA ATT ATT ATC ATG GAT TCT AAA ACG G AT TAC CAG GGA TTT CAG      537
Gln Lys Ile Ile Ile Met Asp Ser Lys Thr A sp Tyr Gln Gly Phe Gln
                150                 155                 160

TCG ATG TAC ACG TTC GTC ACA TCT CAT CTA C CT CCC GGT TTT AAT GAA      585
Ser Met Tyr Thr Phe Val Thr Ser His Leu P ro Pro Gly Phe Asn Glu
            165                 170                 175

TAC GAT TTT GTA CCA GAG TCC TTT GAT CGT G AC AAA ACA ATT GCA CTG      633
Tyr Asp Phe Val Pro Glu Ser Phe Asp Arg A sp Lys Thr Ile Ala Leu
            180                 185                 190

ATA ATG AAT TCC TCT GGA TCT ACT GGG TTA C CT AAG GGT GTG GCC CTT      681
Ile Met Asn Ser Ser Gly Ser Thr Gly Leu P ro Lys Gly Val Ala Leu
195                 200                 205                 210

CCG CAT AGA ACT GCC TGC GTC AGA TTC TCG C AT GCC AGA GAT CCT ATT      729
Pro His Arg Thr Ala Cys Val Arg Phe Ser H is Ala Arg Asp Pro Ile
                215                 220                 225

TTT GGC AAT CAA ATC ATT CCG GAT ACT GCG A TT TTA AGT GTT GTT CCA      777
Phe Gly Asn Gln Ile Ile Pro Asp Thr Ala I le Leu Ser Val Val Pro
                230                 235                 240

TTC CAT CAC GGT TTT GGA ATG TTT ACT ACA C TC GGA TAT TTG ATA TGT      825
Phe His His Gly Phe Gly Met Phe Thr Thr L eu Gly Tyr Leu Ile Cys
            245                 250                 255
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
GGA TTT CGA GTC GTC TTA ATG TAT AGA TTT G AA GAA GAG CTG TTT TTA    873
Gly Phe Arg Val Val Leu Met Tyr Arg Phe G lu Glu Glu Leu Phe Leu
        260                 265                 270

CGA TCC CTT CAG GAT TAC AAA ATT CAA AGT G CG TTG CTA GTA CCA ACC    921
Arg Ser Leu Gln Asp Tyr Lys Ile Gln Ser A la Leu Leu Val Pro Thr
275                 280                 285                 290

CTA TTT TCA TTC TTC GCC AAA AGC ACT CTG A TT GAC AAA TAC GAT TTA    969
Leu Phe Ser Phe Phe Ala Lys Ser Thr Leu I le Asp Lys Tyr Asp Leu
                295                 300                 305

TCT AAT TTA CAC GAA ATT GCT TCT GGG GGC G CA CCT CTT TCG AAA GAA   1017
Ser Asn Leu His Glu Ile Ala Ser Gly Gly A la Pro Leu Ser Lys Glu
        310                 315                 320

GTC GGG GAA GCG GTT GCA AAA CGC TTC CAT C TT CCA GGG ATA CGA CAA   1065
Val Gly Glu Ala Val Ala Lys Arg Phe His L eu Pro Gly Ile Arg Gln
        325                 330                 335

GGA TAT GGG CTC ACT GAG ACT ACA TCA GCT A TT CTG ATT ACA CCC GAG   1113
Gly Tyr Gly Leu Thr Glu Thr Thr Ser Ala I le Leu Ile Thr Pro Glu
        340                 345                 350

GGG GAT GAT AAA CCG GGC GCG GTC GGT AAA G TT GTT CCA TTT TTT GAA   1161
Gly Asp Asp Lys Pro Gly Ala Val Gly Lys V al Val Pro Phe Phe Glu
355                 360                 365                 370

GCG AAG GTT GTG GAT CGT GAT ACC GGG AAA A CG CTG GGC GTT ATT CAG   1209
Ala Lys Val Val Asp Arg Asp Thr Gly Lys T hr Leu Gly Val Ile Gln
                375                 380                 385

AGA GGC GAA TTA TGT CTC AGA GGA CCT ATG A TT ATG TCC GGT TAT GTA   1257
Arg Gly Glu Leu Cys Val Arg Gly Pro Met I le Met Ser Gly Tyr Val
        390                 395                 400

AAC AAT CCG GAA GCG ACC AAC GCC TTG ATT G AC AAG GAT GGA TGG CTA   1305
Asn Asn Pro Glu Ala Thr Asn Ala Leu Ile A sp Lys Asp Gly Trp Leu
        405                 410                 415

CAT TCT GGA GAC ATA GCT TAC TGG GAC GAA G AC GAA CAC TTC TTC ATA   1353
His Ser Gly Asp Ile Ala Tyr Trp Asp Glu A sp Glu His Phe Phe Ile
        420                 425                 430
```

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
GTT GAC CGC TTG AAG TCT TTA ATT AAA TAC A AA GGA TAT CAG GTG GCC    1401
Val Asp Arg Leu Lys Ser Leu Ile Lys Tyr L ys Gly Tyr Gln Val Ala
435             440             445             450

CCC GCT GAA TTG GAA TCG ATA TTG TTA CAA C AC CCC AAC ATC TTC GAC    1449
Pro Ala Glu Leu Glu Ser Ile Leu Leu Gln H is Pro Asn Ile Phe Asp
                455             460             465

GCG GGC GTG GCA GGT CTT CCC GAC GAT GAC G CC GGT GAA CTT CCC GCC    1497
Ala Gly Val Ala Gly Leu Pro Asp Asp Asp A la Gly Glu Leu Pro Ala
            470             475             480

GCC GTT GTT GTT TTG GAG CAC GGA AAG ACG A TG ACG GAA AAA GAG ATC    1545
Ala Val Val Val Leu Glu His Gly Lys Thr M et Thr Glu Lys Glu Ile
        485             490             495

GTG GAT TAC GTG GCC AGT CAA GTA ACA ACC G CG AAA AAG TTG CGC GGA    1593
Val Asp Tyr Val Ala Ser Gln Val Thr Thr A la Lys Lys Leu Arg Gly
    500             505             510

GGA GTT GTG TTT GTG GAC GAA GTA CCG AAA G GT CTT ACC GGA AAA CTC    1641
Gly Val Val Phe Val Asp Glu Val Pro Lys G ly Leu Thr Gly Lys Leu
515             520             525             530

GAC GCA AGA AAA ATC AGA GAG ATC CTC ATA A AG GCC AAG AAG GGC GGA    1689
Asp Ala Arg Lys Ile Arg Glu Ile Leu Ile L ys Ala Lys Lys Gly Gly
            535             540             545

AAG TCC AAA TTG TAAAATGTAA CTGTATTCAG CGATGACGAA A TTCTTAGCT        1741
Lys Ser Lys Leu
            550

ATTGTAATAT TATATGCAAA TTGATGAATG GTAATTTTGT AATTGTCGGT C ACTGTACTA  1801
```

Page 28 of 52

UNITED STATES PATENT AND TRADEMARK OFFICE
CERTIFICATE OF CORRECTION

| | |
|---|---|
| PATENT NO. | : 6,552,179 B1 |
| APPLICATION NO. | : 08/478205 |
| DATED | : April 22, 2003 |
| INVENTOR(S) | : Keith V. Wood and Monika G. Wood |

It is certified that error appears in the above-identified patent and that said Letters Patent is hereby corrected as shown below:

```
TTTTAACGAA TAATAAAATC AGGTATAGGT AACTAAA                                    1838

(2) INFORMATION FOR SEQ ID NO:10:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:10:

Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
            35                  40                  45

Val Asn Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
 65                 70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
            115                 120                 125
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Ser Lys Lys Gly Leu Gln Lys Ile Leu Asn Val Gln Lys Lys Leu Pro
    130                 135             140

Ile Ile Gln Lys Ile Ile Ile Met Asp Ser Lys Thr Asp Tyr Gln Gly
145                 150             155                 160

Phe Gln Ser Met Tyr Thr Phe Val Thr Ser His Leu Pro Pro Gly Phe
                165             170                 175

Asn Glu Tyr Asp Phe Val Pro Glu Ser Phe Asp Arg Asp Lys Thr Ile
            180             185             190

Ala Leu Ile Met Asn Ser Ser Gly Ser Thr Gly Leu Pro Lys Gly Val
            195             200             205

Ala Leu Pro His Arg Thr Ala Cys Val Arg Phe Ser His Ala Arg Asp
        210             215             220

Pro Ile Phe Gly Asn Gln Ile Ile Pro Asp Thr Ala Ile Leu Ser Val
225             230             235             240

Val Pro Phe His His Gly Phe Gly Met Phe Thr Thr Leu Gly Tyr Leu
            245             250             255

Ile Cys Gly Phe Arg Val Val Leu Met Tyr Arg Phe Glu Glu Glu Leu
            260             265             270

Phe Leu Arg Ser Leu Gln Asp Tyr Lys Ile Gln Ser Ala Leu Leu Val
        275             280             285

Pro Thr Leu Phe Ser Phe Phe Ala Lys Ser Thr Leu Ile Asp Lys Tyr
    290             295             300

Asp Leu Ser Asn Leu His Glu Ile Ala Ser Gly Gly Ala Pro Leu Ser
305             310             315             320

Lys Glu Val Gly Glu Ala Val Ala Lys Arg Phe His Leu Pro Gly Ile
            325             330             335

Arg Gln Gly Tyr Gly Leu Thr Glu Thr Thr Ser Ala Ile Leu Ile Thr
            340             345             350
```

UNITED STATES PATENT AND TRADEMARK OFFICE
CERTIFICATE OF CORRECTION

PATENT NO.        : 6,552,179 B1
APPLICATION NO. : 08/478205
DATED             : April 22, 2003
INVENTOR(S)       : Keith V. Wood and Monika G. Wood It is certified that error appears in the above-identified patent and that said Letters Patent is hereby corrected as shown below:

```
Pro Glu Gly Asp Asp Lys Pro Gly Ala Val Gly Lys Val Val Pro Phe
        355                 360                 365
Phe Glu Ala Lys Val Val Asp Arg Asp Thr Gly Lys Thr Leu Gly Val
        370                 375                 380
Ile Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
            435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Ile Lys Ala Lys Lys
    530                 535                 540
Gly Gly Lys Ser Lys Leu
545                 550
```

UNITED STATES PATENT AND TRADEMARK OFFICE
CERTIFICATE OF CORRECTION

PATENT NO.         : 6,552,179 B1
APPLICATION NO.    : 08/478205
DATED              : April 22, 2003
INVENTOR(S)        : Keith V. Wood and Monika G. Wood It is certified that error appears in the above-identified patent and that said Letters Patent is hereby corrected as shown below:

```
(2) INFORMATION FOR SEQ ID NO:11:

(i) SEQUENCE CHARACTERISTICS:
        (A) LENGTH: 1644 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1644

(ix) FEATURE:
        (A) NAME/KEY: mat_ peptide
        (B) LOCATION: 1..1644

(xi) SEQUENCE DESCRIPTION: SEQ ID NO:11:

ATG GAA AAC ATG GAA AAC GAT GAA AAT ATT G TA GTT GGA CCT AAA CCG         48
    Met Glu Asn Met Glu Asn Asp Glu Asn Ile V al Val Gly Pro Lys Pro
    1               5                   10                  15

TTT TAC CCT ATC GAA GAG GGA TCT GCT GGA A CA CAA TTA CGC AAA TAC         96
    Phe Tyr Pro Ile Glu Glu Gly Ser Ala Gly T hr Gln Leu Arg Lys Tyr
                    20                  25                  30

ATG GAG CGA TAT GCA AAA CTT GGC GCA ATT G CT TTT ACA AAT GCA GTT        144
    Met Glu Arg Tyr Ala Lys Leu Gly Ala Ile A la Phe Thr Asn Ala Val
                35                  40                  45

ACT GGT GTT GAT TAT TCT TAC GCC GAA TAC T TG GAG AAA TCA TGT TGT        192
    Thr Gly Val Asp Tyr Ser Tyr Ala Glu Tyr L eu Glu Lys Ser Cys Cys
                50                  55                  60

CTA GGA AAA GCT TTG CAA AAT TAT GGT TTG G TT GTT GAT GGC AGA ATT        240
    Leu Gly Lys Ala Leu Gln Asn Tyr Gly Leu V al Val Asp Gly Arg Ile
    65                  70                  75                  80
```

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
GCG TTA TGC AGT GAA AAC TGT GAA GAA TTT T TT ATT CCT GTA ATA GCC       288
Ala Leu Cys Ser Glu Asn Cys Glu Glu Phe P he Ile Pro Val Ile Ala
                85                  90                  95

GGA CTG TTT ATA GGT GTA GGT GTT GCA CCC A CT AAT GAG ATT TAC ACT       336
Gly Leu Phe Ile Gly Val Gly Val Ala Pro T hr Asn Glu Ile Tyr Thr
            100                 105                 110

TTA CGT GAA CTG GTT CAC AGT TTA GGT ATC T CT AAA CCA ACA ATT GTA       384
Leu Arg Glu Leu Val His Ser Leu Gly Ile S er Lys Pro Thr Ile Val
            115                 120                 125

TTT AGT TCT AAA AAA GGC TTA GAT AAA GTT A TA ACA GTA CAG AAA ACA       432
Phe Ser Ser Lys Lys Gly Leu Asp Lys Val I le Thr Val Gln Lys Thr
            130                 135                 140

GTA ACT ACT ATT AAA ACC ATT GTT ATA CTA G AT AGC AAA GTT GAT TAT       480
Val Thr Thr Ile Lys Thr Ile Val Ile Leu A sp Ser Lys Val Asp Tyr
145             150                 155                 160

CGA GGA TAT CAA TGT CTG GAC ACC TTT ATA A AA AGA AAC ACT CCA CCA       528
Arg Gly Tyr Gln Cys Leu Asp Thr Phe Ile L ys Arg Asn Thr Pro Pro
                165                 170                 175

GGT TTT CAA GCA TCC AGT TTC AAA ACT GTG G AA GTT GAC CGT AAA GAA       576
Gly Phe Gln Ala Ser Ser Phe Lys Thr Val G lu Val Asp Arg Lys Glu
            180                 185                 190

CAA GTT GCT CTT ATA ATG AAC TCT TCG GGT T CT ACC GGT TTG CCA AAA       624
Gln Val Ala Leu Ile Met Asn Ser Ser Gly S er Thr Gly Leu Pro Lys
            195                 200                 205

GGC GTA CAA CTT ACT CAC GAA AAT ACA GTC A CT AGA TTT TCT CAT GCT       672
Gly Val Gln Leu Thr His Glu Asn Thr Val T hr Arg Phe Ser His Ala
            210                 215                 220
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
AGA GAT CCG ATT TAT GGT AAC CAA GTT TCA C CA GGC ACC GCT GTT TTA         720
Arg Asp Pro Ile Tyr Gly Asn Gln Val Ser P ro Gly Thr Ala Val Leu
225             230             235             240

ACT GTC GTT CCA TTC CAT CAT GGT TTT GGT A TG TTC ACT ACT CTA GGG         768
Thr Val Val Pro Phe His His Gly Phe Gly M et Phe Thr Thr Leu Gly
                245             250             255

TAT TTA ATT TGT GGT TTT CGT GTT GTA ATG T TA ACA AAA TTC GAT GAA         816
Tyr Leu Ile Cys Gly Phe Arg Val Val Met L eu Thr Lys Phe Asp Glu
            260             265             270

GAA ACA TTT TTA AAA ACT CTA CAA GAT TAT A AA TGT ACA AGT GTT ATT         864
Glu Thr Phe Leu Lys Thr Leu Gln Asp Tyr L ys Cys Thr Ser Val Ile
        275             280             285

CTT GTA CCG ACC TTG TTT GCA ATT CTC AAC A AA AGT GAA TTA CTC AAT         912
Leu Val Pro Thr Leu Phe Ala Ile Leu Asn L ys Ser Glu Leu Leu Asn
    290             295             300

AAA TAC GAT TTG TCA AAT TTA GTT GAG ATT G CA TCT GGC GGA GCA CCT         960
Lys Tyr Asp Leu Ser Asn Leu Val Glu Ile A la Ser Gly Gly Ala Pro
305             310             315             320

TTA TCA AAA GAA GTT GGT GAA GCT CTT GCT A GA CGC TTT AAT CTT CCC        1008
Leu Ser Lys Glu Val Gly Glu Ala Leu Ala A rg Arg Phe Asn Leu Pro
            325             330             335

GGT GTT CGT CAA GGT TAT GGT TTA ACA GAA A CA ACA TCT GCC ATT ATT        1056
Gly Val Arg Gln Gly Tyr Gly Leu Thr Glu T hr Thr Ser Ala Ile Ile
        340             345             350

ATT ACA CCA GAA GGA GAC GAT AAA CCA GGA G CT TCT GGA AAA GTC GTG        1104
Ile Thr Pro Glu Gly Asp Asp Lys Pro Gly A la Ser Gly Lys Val Val
    355             360             365

CCG TTG TTT AAA GCA AAA GTT ATT GAT CTT G AT ACC AAA AAA TCT TTA        1152
Pro Leu Phe Lys Ala Lys Val Ile Asp Leu A sp Thr Lys Lys Ser Leu
370             375             380

GGT CCT AAC AGA CGT GGA GAA GTT TGT GTT A AA GGA CCT ATG CTT ATG        1200
Gly Pro Asn Arg Arg Gly Glu Val Cys Val L ys Gly Pro Met Leu Met
385             390             395             400
```

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
AAA GGT TAT GTA AAT AAT CCA GAA GCA ACA A AA GAA CTT ATT GAC GAA    1248
Lys Gly Tyr Val Asn Asn Pro Glu Ala Thr L ys Glu Leu Ile Asp Glu
            405                 410                 415

GAA GGT TGG CTG CAC ACC GGA GAT ATT GGA T AT TAT GAT GAA GAA AAA    1296
Glu Gly Trp Leu His Thr Gly Asp Ile Gly T yr Tyr Asp Glu Glu Lys
            420                 425                 430

CAT TTC TTT ATT GTC GAT CGT TTG AAG TCT T TA ATC AAA TAC AAA GGA    1344
His Phe Phe Ile Val Asp Arg Leu Lys Ser L eu Ile Lys Tyr Lys Gly
            435                 440                 445

TAC CAA GTA CCA CCT GCC GAA TTA GAA TCC G TT CTT TGG CAA CAT CCA    1392
Tyr Gln Val Pro Pro Ala Glu Leu Glu Ser V al Leu Trp Gln His Pro
            450                 455                 460

TCT ATC TTT GAT GCT GGT GTT GCC GGC GTT C CT GAT CCT GTA GCT GGC    1440
Ser Ile Phe Asp Ala Gly Val Ala Gly Val P ro Asp Pro Val Ala Gly
465             470                 475                 480

GAG CTT CCA GGA GCC GTT GTT GTA CTG GAA A GC GGA AAA AAT ATG ACC    1488
Glu Leu Pro Gly Ala Val Val Val Leu Glu S er Gly Lys Asn Met Thr
            485                 490                 495

GAA AAA GAA GTA ATG GAT TAT GTT GCA AGT C AA GTT TCA AAT GCA AAA    1536
Glu Lys Glu Val Met Asp Tyr Val Ala Ser G ln Val Ser Asn Ala Lys
            500                 505                 510

CGT TTA CGT GGT GGT GTT CGT TTT GTG GAT G AA GTA CCT AAA GGT CTT    1584
Arg Leu Arg Gly Gly Val Arg Phe Val Asp G lu Val Pro Lys Gly Leu
            515                 520                 525

ACT GGA AAA ATT GAC GGC AGA GCA ATT AGA G AA ATC CTT AAG AAA CCA    1632
Thr Gly Lys Ile Asp Gly Arg Ala Ile Arg G lu Ile Leu Lys Lys Pro
            530                 535                 540

GTT GCT AAG ATG                                                     1644
Val Ala Lys Met
545
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
(2) INFORMATION FOR SEQ ID NO:12:

(i) SEQUENCE CHARACTERISTICS:
        (A) LENGTH: 548 amino acids
        (B) TYPE: amino acid
        (D) TOPOLOGY: linear (ii) MOLECULE TYPE: protein (xi) SEQUENCE DESCRIPTION: SEQ ID NO:12:

Met Glu Asn Met Glu Asn Asp Glu Asn Ile V al Val Gly Pro Lys Pro
 1               5                  10                  15

Phe Tyr Pro Ile Glu Glu Gly Ser Ala Gly T hr Gln Leu Arg Lys Tyr
             20                  25                  30

Met Glu Arg Tyr Ala Lys Leu Gly Ala Ile A la Phe Thr Asn Ala Val
         35                  40                  45

Thr Gly Val Asp Tyr Ser Tyr Ala Glu Tyr L eu Glu Lys Ser Cys Cys
     50                  55                  60

Leu Gly Lys Ala Leu Gln Asn Tyr Gly Leu V al Val Asp Gly Arg Ile
 65                  70                  75                  80

Ala Leu Cys Ser Glu Asn Cys Glu Glu Phe P he Ile Pro Val Ile Ala
                 85                  90                  95

Gly Leu Phe Ile Gly Val Gly Val Ala Pro T hr Asn Glu Ile Tyr Thr
            100                 105                 110

Leu Arg Glu Leu Val His Ser Leu Gly Ile S er Lys Pro Thr Ile Val
            115                 120                 125

Phe Ser Ser Lys Lys Gly Leu Asp Lys Val I le Thr Val Gln Lys Thr
        130                 135                 140
```

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
Val Thr Thr Ile Lys Thr Ile Val Ile Leu A sp Ser Lys Val Asp Tyr
145                 150                 155                 160

Arg Gly Tyr Gln Cys Leu Asp Thr Phe Ile L ys Arg Asn Thr Pro Pro
                165                 170                 175

Gly Phe Gln Ala Ser Ser Phe Lys Thr Val G lu Val Asp Arg Lys Glu
            180                 185                 190

Gln Val Ala Leu Ile Met Asn Ser Ser Gly S er Thr Gly Leu Pro Lys
        195                 200                 205

Gly Val Gln Leu Thr His Glu Asn Thr Val T hr Arg Phe Ser His Ala
         210                 215                 220

Arg Asp Pro Ile Tyr Gly Asn Gln Val Ser P ro Gly Thr Ala Val Leu
225                 230                 235                 240

Thr Val Val Pro Phe His His Gly Phe Gly M et Phe Thr Thr Leu Gly
                245                 250                 255

Tyr Leu Ile Cys Gly Phe Arg Val Val Met L eu Thr Lys Phe Asp Glu
                260                 265                 270

Glu Thr Phe Leu Lys Thr Leu Gln Asp Tyr L ys Cys Thr Ser Val Ile
            275                 280                 285

Leu Val Pro Thr Leu Phe Ala Ile Leu Asn L ys Ser Glu Leu Leu Asn
        290                 295                 300

Lys Tyr Asp Leu Ser Asn Leu Val Glu Ile A la Ser Gly Gly Ala Pro
305                 310                 315                 320

Leu Ser Lys Glu Val Gly Glu Ala Leu Ala A rg Arg Phe Asn Leu Pro
                325                 330                 335

Gly Val Arg Gln Gly Tyr Gly Leu Thr Glu T hr Thr Ser Ala Ile Ile
            340                 345                 350

Ile Thr Pro Glu Gly Asp Asp Lys Pro Gly A la Ser Gly Lys Val Val
        355                 360                 365
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Pro Leu Phe Lys Ala Lys Val Ile Asp Leu A sp Thr Lys Lys Ser Leu
    370             375                 380

Gly Pro Asn Arg Arg Gly Glu Val Cys Val L ys Gly Pro Met Leu Met
385             390                 395                     400

Lys Gly Tyr Val Asn Asn Pro Glu Ala Thr L ys Glu Leu Ile Asp Glu
                405             410                     415

Glu Gly Trp Leu His Thr Gly Asp Ile Gly T yr Tyr Asp Glu Glu Lys
            420             425                     430

His Phe Phe Ile Val Asp Arg Leu Lys Ser L eu Ile Lys Tyr Lys Gly
            435             440                     445

Tyr Gln Val Pro Pro Ala Glu Leu Glu Ser V al Leu Trp Gln His Pro
    450             455                 460

Ser Ile Phe Asp Ala Gly Val Ala Gly Val P ro Asp Pro Val Ala Gly
465             470                 475                     480

Glu Leu Pro Gly Ala Val Val Leu Glu Ser G ly Lys Asn Met Thr
                485             490                     495

Glu Lys Glu Val Met Asp Tyr Val Ala Ser G ln Val Ser Asn Ala Lys
            500             505                     510

Arg Leu Arg Gly Gly Val Arg Phe Val Asp G lu Val Pro Lys Gly Leu
            515             520                     525

Thr Gly Lys Ile Asp Gly Arg Ala Ile Arg G lu Ile Leu Lys Lys Pro
            530             535                     540

Val Ala Lys Met
545
```

UNITED STATES PATENT AND TRADEMARK OFFICE
CERTIFICATE OF CORRECTION

PATENT NO.       : 6,552,179 B1
APPLICATION NO.  : 08/478205
DATED            : April 22, 2003
INVENTOR(S)      : Keith V. Wood and Monika G. Wood It is certified that error appears in the above-identified patent and that said Letters Patent is hereby corrected as shown below:

```
(2) INFORMATION FOR SEQ ID NO:13:

(i) SEQUENCE CHARACTERISTICS:
        (A) LENGTH: 1644 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1644

(ix) FEATURE:
        (A) NAME/KEY: mat_peptide
        (B) LOCATION: 1..1644

(xi) SEQUENCE DESCRIPTION: SEQ ID NO:13:

ATG GAA AAC ATG GAG AAC GAT GAA AAT ATT G TG GTA GGT CCT GAA CCA        48
Met Glu Asn Met Glu Asn Asp Glu Asn Ile V al Val Gly Pro Glu Pro
 1               5                  10                  15

TTT TAC CCT ATT GAA GAG GGA TCT GCT GGA G CA CAA TTG CGC AAG TAT        96
Phe Tyr Pro Ile Glu Glu Gly Ser Ala Gly A la Gln Leu Arg Lys Tyr
                20                  25                  30

ATG GAT CGA TAT GCA AAA CTT GGA GCA ATT G CT TTT ACT AAC GCA CTT       144
Met Asp Arg Tyr Ala Lys Leu Gly Ala Ile A la Phe Thr Asn Ala Leu
                35                  40                  45

ACC GGT GTC GAT TAT ACG TAC GCC GAA TAC T TA GAA AAA TCA TGC TGT       192
Thr Gly Val Asp Tyr Thr Tyr Ala Glu Tyr L eu Glu Lys Ser Cys Cys
        50                  55                  60

CTA GGA GAG GCT TTA AAG AAT TAT GGT TTG G TT GTT GAT GGA AGA ATT       240
Leu Gly Glu Ala Leu Lys Asn Tyr Gly Leu V al Val Asp Gly Arg Ile
 65                 70                  75                  80

GCG TTA TGC AGT GAA AAC TGT GAA GAA TTC T TT ATT CCT GTA TTA GCC       288
Ala Leu Cys Ser Glu Asn Cys Glu Glu Phe P he Ile Pro Val Leu Ala
                85                  90                  95
```

Page 39 of 52

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
GGT TTA TTT ATA GGT GTC GGT GTG GCT CCA A CT AAT GAG ATT TAC ACT      336
Gly Leu Phe Ile Gly Val Gly Val Ala Pro T hr Asn Glu Ile Tyr Thr
            100             105             110

CTA CGT GAA TTG GTT CAC AGT TTA GGC ATC T CT AAG CCA ACA ATT GTA      384
Leu Arg Glu Leu Val His Ser Leu Gly Ile S er Lys Pro Thr Ile Val
        115             120             125

TTT AGT TCT AAA AAA GGA TTA GAT AAA GTT A TA ACT GTA CAA AAA ACG      432
Phe Ser Ser Lys Lys Gly Leu Asp Lys Val I le Thr Val Gln Lys Thr
        130             135             140

GTA ACT GCT ATT AAA ACC ATT GTT ATA TTG G AC AGC AAA GTG GAT TAT      480
Val Thr Ala Ile Lys Thr Ile Val Ile Leu A sp Ser Lys Val Asp Tyr
145             150             155             160

AGA GGT TAT CAA TCC ATG GAC AAC TTT ATT A AA AAA AAC ACT CCA CAA      528
Arg Gly Tyr Gln Ser Met Asp Asn Phe Ile L ys Lys Asn Thr Pro Gln
            165             170             175

GGT TTC AAA GGA TCA AGT TTT AAA ACT GTA G AA GTT AAC CGC AAA GAA      576
Gly Phe Lys Gly Ser Ser Phe Lys Thr Val G lu Val Asn Arg Lys Glu
            180             185             190

CAA GTT GCT CTT ATA ATG AAC TCT TCG GGT T CA ACC GGT TTG CCA AAA      624
Gln Val Ala Leu Ile Met Asn Ser Ser Gly S er Thr Gly Leu Pro Lys
            195             200             205

GGT GTG CAA CTT ACT CAT GAA AAT GCA GTC A CT AGA TTT TCT CAC GCT      672
Gly Val Gln Leu Thr His Glu Asn Ala Val T hr Arg Phe Ser His Ala
        210             215             220

AGA GAT CCA ATT TAT GGA AAC CAA GTT TCA C CA GGC ACG GCT ATT TTA      720
Arg Asp Pro Ile Tyr Gly Asn Gln Val Ser P ro Gly Thr Ala Ile Leu
225             230             235             240
```

UNITED STATES PATENT AND TRADEMARK OFFICE
CERTIFICATE OF CORRECTION

PATENT NO.      : 6,552,179 B1
APPLICATION NO. : 08/478205
DATED           : April 22, 2003
INVENTOR(S)     : Keith V. Wood and Monika G. Wood It is certified that error appears in the above-identified patent and that said Letters Patent is hereby corrected as shown below:

```
ACT GTA GTA CCA TTC CAT CAT GGT TTT GGT A TG TTT ACT ACT TTA GGC      768
Thr Val Val Pro Phe His His Gly Phe Gly M et Phe Thr Thr Leu Gly
            245                 250                 255

TAT CTA ACT TGT GGT TTT CGT ATT GTC ATG T TA ACG AAA TTT GAC GAA      816
Tyr Leu Thr Cys Gly Phe Arg Ile Val Met L eu Thr Lys Phe Asp Glu
            260                 265                 270

GAG ACT TTT TTA AAA ACA CTG CAA GAT TAC A AA TGT TCA AGC GTT ATT      864
Glu Thr Phe Leu Lys Thr Leu Gln Asp Tyr L ys Cys Ser Ser Val Ile
        275                 280                 285

CTT GTA CCG ACT TTG TTT GCA ATT CTT AAT A GA AGT GAA TTA CTC GAT      912
Leu Val Pro Thr Leu Phe Ala Ile Leu Asn A rg Ser Glu Leu Leu Asp
        290                 295                 300

AAA TAT GAT TTA TCA AAT TTA GTT GAA ATT G CA TCT GGC GGA GCA CCT      960
Lys Tyr Asp Leu Ser Asn Leu Val Glu Ile A la Ser Gly Gly Ala Pro
305                 310                 315                 320

TTA TCT AAA GAA ATT GGT GAA GCT GTT GCT A GA CGT TTT AAT TTA CCG     1008
Leu Ser Lys Glu Ile Gly Glu Ala Val Ala A rg Arg Phe Asn Leu Pro
            325                 330                 335

GGT GTT CGT CAA GGC TAT GGT TTA ACA GAA A CA ACC TCT GCA ATT ATT     1056
Gly Val Arg Gln Gly Tyr Gly Leu Thr Glu T hr Thr Ser Ala Ile Ile
            340                 345                 350

ATC ACA CCG GAA GGC GAT GAT AAA CCA GGT G CT TCT GGA AAA GTT GTG     1104
Ile Thr Pro Glu Gly Asp Asp Lys Pro Gly A la Ser Gly Lys Val Val
            355                 360                 365

CCA TTA TTT AAA GCA AAA GTT ATC GAT CTT G AT ACT AAA AAA ACT TTG     1152
Pro Leu Phe Lys Ala Lys Val Ile Asp Leu A sp Thr Lys Lys Thr Leu
        370                 375                 380

GGC CCG AAC AGA CGT GGA GAA GTT TGT GTA A AG GGT CCT ATG CTT ATG     1200
Gly Pro Asn Arg Arg Gly Glu Val Cys Val L ys Gly Pro Met Leu Met
385                 390                 395                 400
```

UNITED STATES PATENT AND TRADEMARK OFFICE
CERTIFICATE OF CORRECTION

PATENT NO.       : 6,552,179 B1
APPLICATION NO.  : 08/478205
DATED            : April 22, 2003
INVENTOR(S)      : Keith V. Wood and Monika G. Wood It is certified that error appears in the above-identified patent and that said Letters Patent is hereby corrected as shown below:

```
AAA GGT TAT GTA GAT AAT CCA GAA GCA ACA A GA GAA ATC ATA GAT GAA            1248
Lys Gly Tyr Val Asp Asn Pro Glu Ala Thr A rg Glu Ile Ile Asp Glu
                405                     410             415

GAA GGT TGG TTG CAC ACA GGA GAT ATT GGG T AT TAC GAT GAA GAA AAA            1296
Glu Gly Trp Leu His Thr Gly Asp Ile Gly T yr Tyr Asp Glu Glu Lys
                420                     425             430

CAT TTC TTT ATC GTG GAT CGT TTG AAG TCT T TA ATC AAA TAC AAA GGA            1344
His Phe Phe Ile Val Asp Arg Leu Lys Ser L eu Ile Lys Tyr Lys Gly
                435                     440             445

TAT CAA GTA CCA CCT GCT GAA TTA GAA TCT G TT CTT TTG CAA CAT CCA            1392
Tyr Gln Val Pro Pro Ala Glu Leu Glu Ser V al Leu Leu Gln His Pro
                450                     455             460

AAT ATT TTT GAT GCC GGC GTT GCT GGC GTT C CA GAT CCT ATA GCT GGT            1440
Asn Ile Phe Asp Ala Gly Val Ala Gly Val P ro Asp Pro Ile Ala Gly
465                     470             475             480

GAG CTT CCG GGA GCT GTT GTT GTA CTT GAA A AA GGA AAA TCT ATG ACT            1488
Glu Leu Pro Gly Ala Val Val Val Leu Glu L ys Gly Lys Ser Met Thr
                485                     490             495

GAA AAA GAA GTA ATG GAT TAC GTT GCT AGT C AA GTT TCA AAT GCA AAA            1536
Glu Lys Glu Val Met Asp Tyr Val Ala Ser G ln Val Ser Asn Ala Lys
                500                     505             510

CGT TTG CGT GGT GGT GTC CGT TTT GTG GAC G AA GTA CCT AAA GGT CTC            1584
Arg Leu Arg Gly Gly Val Arg Phe Val Asp G lu Val Pro Lys Gly Leu
                515                     520             525

ACT GGT AAA ATT GAC GGT AAA GCA ATT AGA G AA ATA CTG AAG AAA CCA            1632
Thr Gly Lys Ile Asp Gly Lys Ala Ile Arg G lu Ile Leu Lys Lys Pro
                530                     535             540

GTT GCT AAG ATG                                                             1644
Val Ala Lys Met
545
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
(2) INFORMATION FOR SEQ ID NO:14:

(i) SEQUENCE CHARACTERISTICS:
        (A) LENGTH: 548 amino acids
        (B) TYPE: amino acid
        (D) TOPOLOGY: linear (ii) MOLECULE TYPE: protein (xi) SEQUENCE DESCRIPTION: SEQ ID NO:14:

Met Glu Asn Met Glu Asn Asp Glu Asn Ile Val Val Gly Pro Glu Pro
 1               5                  10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
            85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
            165                 170                 175
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Gly Phe Lys Gly Ser Ser Phe Lys Thr Val G lu Val Asn Arg Lys Glu
            180                 185                 190
Gln Val Ala Leu Ile Met Asn Ser Ser Gly S er Thr Gly Leu Pro Lys
            195             200             205
Gly Val Gln Leu Thr His Glu Asn Ala Val T hr Arg Phe Ser His Ala
            210             215             220
Arg Asp Pro Ile Tyr Gly Asn Gln Val Ser P ro Gly Thr Ala Ile Leu
225             230             235                 240
Thr Val Val Pro Phe His His Gly Phe Gly M et Phe Thr Thr Leu Gly
                245             250                 255
Tyr Leu Thr Cys Gly Phe Arg Ile Val Met L eu Thr Lys Phe Asp Glu
            260             265                 270
Glu Thr Phe Leu Lys Thr Leu Gln Asp Tyr L ys Cys Ser Ser Val Ile
            275             280             285
Leu Val Pro Thr Leu Phe Ala Ile Leu Asn A rg Ser Glu Leu Leu Asp
            290             295             300
Lys Tyr Asp Leu Ser Asn Leu Val Glu Ile A la Ser Gly Gly Ala Pro
305             310             315                 320
Leu Ser Lys Glu Ile Gly Glu Ala Val Ala A rg Arg Phe Asn Leu Pro
            325             330                 335
Gly Val Arg Gln Gly Tyr Gly Leu Thr Glu T hr Thr Ser Ala Ile Ile
            340             345                 350
Ile Thr Pro Glu Gly Asp Asp Lys Pro Gly A la Ser Gly Lys Val Val
            355             360             365
Pro Leu Phe Lys Ala Lys Val Ile Asp Leu A sp Thr Lys Lys Thr Leu
            370             375             380
Gly Pro Asn Arg Arg Gly Glu Val Cys Val L ys Gly Pro Met Leu Met
385             390             395                 400
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
    Lys Gly Tyr Val Asp Asn Pro Glu Ala Thr Arg Glu Ile Ile Asp Glu
                    405                 410                 415

Glu Gly Trp Leu His Thr Gly Asp Ile Gly Tyr Tyr Asp Glu Glu Lys
                420                 425                 430

His Phe Phe Ile Val Asp Arg Leu Lys Ser Leu Ile Lys Tyr Lys Gly
                435                 440                 445

Tyr Gln Val Pro Pro Ala Glu Leu Glu Ser Val Leu Leu Gln His Pro
        450                 455                 460

Asn Ile Phe Asp Ala Gly Val Ala Gly Val Pro Asp Pro Ile Ala Gly
    465                 470                 475                 480

Glu Leu Pro Gly Ala Val Val Val Leu Glu Lys Gly Lys Ser Met Thr
                    485                 490                 495

Glu Lys Glu Val Met Asp Tyr Val Ala Ser Gln Val Ser Asn Ala Lys
                500                 505                 510

Arg Leu Arg Gly Gly Val Arg Phe Val Asp Glu Val Pro Lys Gly Leu
                515                 520                 525

Thr Gly Lys Ile Asp Gly Lys Ala Ile Arg Glu Ile Leu Lys Lys Pro
        530                 535                 540

Val Ala Lys Met
    545

(2) INFORMATION FOR SEQ ID NO:15:

(i) SEQUENCE CHARACTERISTICS:
            (A) LENGTH: 2010 base pairs
            (B) TYPE: nucleic acid
            (C) STRANDEDNESS: single
            (D) TOPOLOGY: linear
```

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
        (ix) FEATURE:
             (A) NAME/KEY: CDS
             (B) LOCATION: 69..1713

(ix) FEATURE:
             (A) NAME/KEY: mat_peptide
             (B) LOCATION: 69..1713

(xi) SEQUENCE DESCRIPTION: SEQ ID NO:15:

GGAATTCGGC ACGAGGTTAC AATTACAACT TCGAAGTCCC TAAACGGTAG A GGAAAAGTT        60

TTTGAAAA ATG GAA ATG GAA AAG GAG GAG AAT GTT  GTA TAT GGC CCT CTG       110
         Met Glu Met Glu Lys Glu Glu Asn Val  Val Tyr Gly Pro Leu
          1               5                   10

CCA TTC TAC CCC ATT GAA GAA GGA TCA GCT G GA ATT CAG TTG CAT AAG        158
Pro Phe Tyr Pro Ile Glu Glu Gly Ser Ala G ly Ile Gln Leu His Lys
 15              20                 25                   30

TAC ATG CAT CAA TAT GCC AAA CTT GGA GCA A TT GCT TTT AGT AAC GCC        206
Tyr Met His Gln Tyr Ala Lys Leu Gly Ala I le Ala Phe Ser Asn Ala
             35                 40                    45

CTT ACT GGA GTT GAC ATT TCT TAC CAA GAA T AC TTT GAT ATT ACA TGT        254
Leu Thr Gly Val Asp Ile Ser Tyr Gln Glu T yr Phe Asp Ile Thr Cys
         50                 55                    60

CGT TTA GCT GAG GCC ATG AAA AAC TTT GGT A TG AAA CCG GAA GAA CAT        302
Arg Leu Ala Glu Ala Met Lys Asn Phe Gly M et Lys Pro Glu Glu His
         65                 70                    75

ATT GCT TTG TGC AGT GAA AAT TGT GAA GAA T TT TTC ATC CCT GTA CTT        350
Ile Ala Leu Cys Ser Glu Asn Cys Glu Glu P he Phe Ile Pro Val Leu
         80                 85                    90

GCT GGT CTT TAC ATT GGG GTA GCT GTT GCA C CT ACT AAT GAA ATT TAC        398
Ala Gly Leu Tyr Ile Gly Val Ala Val Ala P ro Thr Asn Glu Ile Tyr
 95              100                105                  110

ACA TTG CGT GAA CTT AAT CAT AGT TTG GGC A TC GCA CAA CCA ACT ATT        446
Thr Leu Arg Glu Leu Asn His Ser Leu Gly I le Ala Gln Pro Thr Ile
             115                120                  125
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
GTA TTC AGC TCC AGA AAA GGC TTA CCT AAA G TT TTA GAA GTG CAA AAA      494
Val Phe Ser Ser Arg Lys Gly Leu Pro Lys V al Leu Glu Val Gln Lys
            130                 135                 140

ACA GTT ACA TGC ATC AAA AAA ATT GTT ATT T TA GAT AGT AAA GTA AAC      542
Thr Val Thr Cys Ile Lys Lys Ile Val Ile L eu Asp Ser Lys Val Asn
            145                 150                 155

TTT GGG GGC CAC GAT TGT ATG GAA ACT TTT A TT AAG AAA CAT GTA GAA      590
Phe Gly Gly His Asp Cys Met Glu Thr Phe I le Lys Lys His Val Glu
            160                 165                 170

TTA GGT TTT CAA CCA AGT AGC TTT GTA CCC A TT GAT GTA AAG AAC CGT      638
Leu Gly Phe Gln Pro Ser Ser Phe Val Pro I le Asp Val Lys Asn Arg
175             180                 185                 190

AAA CAA CAC GTT GCT TTG CTT ATG AAT TCT T CT GGC TCT ACT GGT TTA      686
Lys Gln His Val Ala Leu Leu Met Asn Ser S er Gly Ser Thr Gly Leu
            195                 200                 205

CCT AAA GGT GTA CGA ATT ACC CAC GAA GGT G CA GTT ACA AGA TTC TCA      734
Pro Lys Gly Val Arg Ile Thr His Glu Gly A la Val Thr Arg Phe Ser
            210                 215                 220

CAC GCT AAG GAT CCA ATT TAC GGA AAC CAA G TT TCA CCT GGT ACT GCT      782
His Ala Lys Asp Pro Ile Tyr Gly Asn Gln V al Ser Pro Gly Thr Ala
            225                 230                 235

ATT TTA ACT GTC GTT CCG TTC CAT CAT GGA T TT GGA ATG TTT ACC ACT      830
Ile Leu Thr Val Val Pro Phe His His Gly P he Gly Met Phe Thr Thr
    240                 245                 250

TTA GGA TAC TTT GCT TGT GGA TAC CGT GTT G TA ATG TTA ACA AAA TTT      878
Leu Gly Tyr Phe Ala Cys Gly Tyr Arg Val V al Met Leu Thr Lys Phe
255             260                 265                 270

GAT GAA GAA CTA TTT TTG AGA ACT TTG CAA G AT TAT AAG TGT ACC AGT      926
Asp Glu Glu Leu Phe Leu Arg Thr Leu Gln A sp Tyr Lys Cys Thr Ser
            275                 280                 285
```

UNITED STATES PATENT AND TRADEMARK OFFICE
CERTIFICATE OF CORRECTION

| | |
|---|---|
| PATENT NO. | : 6,552,179 B1 |
| APPLICATION NO. | : 08/478205 |
| DATED | : April 22, 2003 |
| INVENTOR(S) | : Keith V. Wood and Monika G. Wood |

It is certified that error appears in the above-identified patent and that said Letters Patent is hereby corrected as shown below:

```
GTT ATT CTG GTA CCA ACG TTA TTT GCT ATT C TC AAC AAG AGT GAA TTG      974
Val Ile Leu Val Pro Thr Leu Phe Ala Ile L eu Asn Lys Ser Glu Leu
            290                 295                 300

ATC GAT AAG TTC GAT TTA TCT AAT CTA ACT G AA ATT GCT TCT GGT GGA     1022
Ile Asp Lys Phe Asp Leu Ser Asn Leu Thr G lu Ile Ala Ser Gly Gly
            305                 310                 315

GCT CCT TTG GCA AAA GAA GTT GGC GAA GCA G TC GCT AGA AGA TTT AAT     1070
Ala Pro Leu Ala Lys Glu Val Gly Glu Ala V al Ala Arg Arg Phe Asn
            320                 325                 330

CTA CCC GGT GTC CGT CAG GGT TAC GGA TTA A CA GAA ACG ACA TCT GCA     1118
Leu Pro Gly Val Arg Gln Gly Tyr Gly Leu T hr Glu Thr Thr Ser Ala
335             340                 345                 350

TTT ATT ATT ACC CCA GAA GGT GAT GAT AAA C CT GGA GCA TCT GGA AAA     1166
Phe Ile Ile Thr Pro Glu Gly Asp Asp Lys P ro Gly Ala Ser Gly Lys
            355                 360                 365

GTA GTA CCC TTA TTC AAA GTA AAA GTT ATT G AT CTT GAC ACT AAA AAA     1214
Val Val Pro Leu Phe Lys Val Lys Val Ile A sp Leu Asp Thr Lys Lys
            370                 375                 380

ACT TTG GGT GTC AAC CGA CGA GGA GAG ATC T GT GTA AAA GGA CCC AGT     1262
Thr Leu Gly Val Asn Arg Arg Gly Glu Ile C ys Val Lys Gly Pro Ser
            385                 390                 395

CTT ATG TTA GGC TAC TCG AAC AAT CCG GAA G CA ACA AGA GAA ACT ATT     1310
Leu Met Leu Gly Tyr Ser Asn Asn Pro Glu A la Thr Arg Glu Thr Ile
            400                 405                 410

GAT GAA GAG GGT TGG TTG CAC ACA GGA GAT A TT GGA TAT TAC GAC GAA     1358
Asp Glu Glu Gly Trp Leu His Thr Gly Asp I le Gly Tyr Tyr Asp Glu
415                 420                 425                 430

GAC GAA CAT TTC TTC ATT GTC GAT CGT TTG A AA TCA TTA ATC AAA TAC     1406
Asp Glu His Phe Phe Ile Val Asp Arg Leu L ys Ser Leu Ile Lys Tyr
            435                 440                 445
```

UNITED STATES PATENT AND TRADEMARK OFFICE
CERTIFICATE OF CORRECTION

| | |
|---|---|
| PATENT NO. | : 6,552,179 B1 |
| APPLICATION NO. | : 08/478205 |
| DATED | : April 22, 2003 |
| INVENTOR(S) | : Keith V. Wood and Monika G. Wood |

It is certified that error appears in the above-identified patent and that said Letters Patent is hereby corrected as shown below:

```
AAG GGG TAC CAG GTA CCA CCT GCT GAA TTG G AA TCC GTT CTT TTG CAA      1454
Lys Gly Tyr Gln Val Pro Pro Ala Glu Leu G lu Ser Val Leu Leu Gln
            450                 455                 460

CAT CCA AAT ATA TTT GAT GCT GGT GTG GCT G GT GTC CCC GAT CCC GAT      1502
His Pro Asn Ile Phe Asp Ala Gly Val Ala G ly Val Pro Asp Pro Asp
            465                 470                 475

GCT GGC GAA CTT CCA GGG GCT GTA GTT GTA A TG GAA AAA GGA AAA ACT      1550
Ala Gly Glu Leu Pro Gly Ala Val Val Val M et Glu Lys Gly Lys Thr
            480                 485                 490

ATG ACT GAA AAG GAA ATT GTG GAT TAT GTT A AT AGT CAA GTA GTG AAC      1598
Met Thr Glu Lys Glu Ile Val Asp Tyr Val A sn Ser Gln Val Val Asn
495                 500                 505                 510

CAC AAA CGT CTG CGT GGT GGC GTT CGT TTT G TG GAT GAA GTA CCA AAA      1646
His Lys Arg Leu Arg Gly Gly Val Arg Phe V al Asp Glu Val Pro Lys
                515                 520                 525

GGT CTA ACT GGT AAA ATT GAT GCT AAA GTA A TT AGA GAA ATT CTT AAG      1694
Gly Leu Thr Gly Lys Ile Asp Ala Lys Val I le Arg Glu Ile Leu Lys
            530                 535                 540

AAA CCA CAA GCC AAG ATG T AAATCAGTCA AAATGCTATT  CATGTAACTA           1743
Lys Pro Gln Ala Lys Met
            545

AACTACTCAT AAGAAGACAA TTTAAAATTA AGTCATTACA CACTTAGTGT T ATATCTCAA    1803

AAGTAGTGGG AGTTTGACAT TTATCTCAAT AATTTATCGA ATGGATGCTT G TATTAGTTT    1863

CTTATTGTTA ATTATAGCTT TAAAGAACGA CTCCTTTAAT ATATATTTAC T TGCATTCCA    1923

ATGGTTATAT TGTAACGGGC ACGTTTCCCT GATATGTGTG AAATATACGT C AATTGCATT    1983

ATTAAAAAAA AAAAAAAAAA AAAAAA                                          2010
```

UNITED STATES PATENT AND TRADEMARK OFFICE
CERTIFICATE OF CORRECTION

PATENT NO.        : 6,552,179 B1
APPLICATION NO.   : 08/478205
DATED             : April 22, 2003
INVENTOR(S)       : Keith V. Wood and Monika G. Wood It is certified that error appears in the above-identified patent and that said Letters Patent is hereby corrected as shown below:

```
(2) INFORMATION FOR SEQ ID NO:16:

(i) SEQUENCE CHARACTERISTICS:
        (A) LENGTH: 548 amino acids
        (B) TYPE: amino acid
        (D) TOPOLOGY: linear (ii) MOLECULE TYPE: protein (xi) SEQUENCE DESCRIPTION: SEQ ID NO:16:

Met Glu Met Glu Lys Glu Glu Asn Val Val Tyr Gly Pro Leu Pro Phe
 1               5                  10                  15

Tyr Pro Ile Glu Glu Gly Ser Ala Gly Ile Gln Leu His Lys Tyr Met
            20                  25                  30

His Gln Tyr Ala Lys Leu Gly Ala Ile Ala Phe Ser Asn Ala Leu Thr
        35                  40                  45

Gly Val Asp Ile Ser Tyr Gln Glu Tyr Phe Asp Ile Thr Cys Arg Leu
    50                  55                  60

Ala Glu Ala Met Lys Asn Phe Gly Met Lys Pro Glu Glu His Ile Ala
65                  70                  75                  80

Leu Cys Ser Glu Asn Cys Glu Glu Phe Phe Ile Pro Val Leu Ala Gly
                85                  90                  95

Leu Tyr Ile Gly Val Ala Val Ala Pro Thr Asn Glu Ile Tyr Thr Leu
            100                 105                 110

Arg Glu Leu Asn His Ser Leu Gly Ile Ala Gln Pro Thr Ile Val Phe
            115                 120                 125

Ser Ser Arg Lys Gly Leu Pro Lys Val Leu Glu Val Gln Lys Thr Val
    130                 135                 140
```

UNITED STATES PATENT AND TRADEMARK OFFICE
CERTIFICATE OF CORRECTION

| | |
|---|---|
| PATENT NO. | : 6,552,179 B1 |
| APPLICATION NO. | : 08/478205 |
| DATED | : April 22, 2003 |
| INVENTOR(S) | : Keith V. Wood and Monika G. Wood |

It is certified that error appears in the above-identified patent and that said Letters Patent is hereby corrected as shown below:

```
Thr Cys Ile Lys Lys Ile Val Ile Leu Asp S er Lys Val Asn Phe Gly
145                 150             155             160

Gly His Asp Cys Met Glu Thr Phe Ile Lys L ys His Val Glu Leu Gly
            165             170             175

Phe Gln Pro Ser Ser Phe Val Pro Ile Asp V al Lys Asn Arg Lys Gln
            180             185             190

His Val Ala Leu Leu Met Asn Ser Ser Gly S er Thr Gly Leu Pro Lys
            195             200             205

Gly Val Arg Ile Thr His Glu Gly Ala Val T hr Arg Phe Ser His Ala
            210             215             220

Lys Asp Pro Ile Tyr Gly Asn Gln Val Ser P ro Gly Thr Ala Ile Leu
225             230             235             240

Thr Val Val Pro Phe His His Gly Phe Gly M et Phe Thr Thr Leu Gly
            245             250             255

Tyr Phe Ala Cys Gly Tyr Arg Val Val Met L eu Thr Lys Phe Asp Glu
            260             265             270

Glu Leu Phe Leu Arg Thr Leu Gln Asp Tyr L ys Cys Thr Ser Val Ile
            275             280             285

Leu Val Pro Thr Leu Phe Ala Ile Leu Asn L ys Ser Glu Leu Ile Asp
            290             295             300

Lys Phe Asp Leu Ser Asn Leu Thr Glu Ile A la Ser Gly Gly Ala Pro
305             310             315             320

Leu Ala Lys Glu Val Gly Glu Ala Val Ala A rg Arg Phe Asn Leu Pro
            325             330             335

Gly Val Arg Gln Gly Tyr Gly Leu Thr Glu T hr Thr Ser Ala Phe Ile
            340             345             350
```

UNITED STATES PATENT AND TRADEMARK OFFICE
CERTIFICATE OF CORRECTION

PATENT NO. : 6,552,179 B1
APPLICATION NO. : 08/478205
DATED : April 22, 2003
INVENTOR(S) : Keith V. Wood and Monika G. Wood It is certified that error appears in the above-identified patent and that said Letters Patent is hereby corrected as shown below:

```
Ile Thr Pro Glu Gly Asp Asp Lys Pro Gly A la Ser Gly Lys Val Val
        355                 360                 365
Pro Leu Phe Lys Val Lys Val Ile Asp Leu A sp Thr Lys Lys Thr Leu
    370                 375                 380
Gly Val Asn Arg Arg Gly Glu Ile Cys Val L ys Gly Pro Ser Leu Met
385                 390                 395                 400
Leu Gly Tyr Ser Asn Asn Pro Glu Ala Thr A rg Glu Thr Ile Asp Glu
                405                 410                 415
Glu Gly Trp Leu His Thr Gly Asp Ile Gly T yr Tyr Asp Glu Asp Glu
            420                 425                 430
His Phe Phe Ile Val Asp Arg Leu Lys Ser L eu Ile Lys Tyr Lys Gly
            435                 440                 445
Tyr Gln Val Pro Pro Ala Glu Leu Glu Ser V al Leu Leu Gln His Pro
        450                 455                 460
Asn Ile Phe Asp Ala Gly Val Ala Gly Val P ro Asp Pro Asp Ala Gly
465                 470                 475                 480
Glu Leu Pro Gly Ala Val Val Val Met Glu L ys Gly Lys Thr Met Thr
                485                 490                 495
Glu Lys Glu Ile Val Asp Tyr Val Asn Ser G ln Val Val Asn His Lys
                500                 505                 510
Arg Leu Arg Gly Gly Val Arg Phe Val Asp G lu Val Pro Lys Gly Leu
            515                 520                 525
Thr Gly Lys Ile Asp Ala Lys Val Ile Arg G lu Ile Leu Lys Lys Pro
        530                 535                 540
Gln Ala Lys Met                                                 --
545
```

Signed and Sealed this

Twenty Second Day of April, 2008

JON W. DUDAS
*Director of the United States Patent and Trademark Office*